(12) United States Patent
Jogasaki et al.

(10) Patent No.: US 10,265,131 B2
(45) Date of Patent: Apr. 23, 2019

(54) SURGICAL INSTRUMENT

(71) Applicant: OLYMPUS CORPORATION, Tokyo (JP)

(72) Inventors: Shuya Jogasaki, Tokyo (JP); Toshihiro Yoshii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 258 days.

(21) Appl. No.: 15/086,515

(22) Filed: Mar. 31, 2016

(65) Prior Publication Data
US 2016/0213438 A1 Jul. 28, 2016

Related U.S. Application Data

(63) Continuation of application No. PCT/JP2014/078901, filed on Oct. 30, 2014.

(30) Foreign Application Priority Data

Oct. 31, 2013 (JP) .................................. 2013-226454

(51) Int. Cl.
*A61B 34/00* (2016.01)
*A61B 17/29* (2006.01)
(Continued)

(52) U.S. Cl.
CPC ............... *A61B 34/71* (2016.02); *A61B 1/00* (2013.01); *A61B 1/0016* (2013.01);
(Continued)

(58) Field of Classification Search
CPC . A61B 1/00147; A61B 1/0016; A61B 1/0057; A61B 17/00234; A61B 17/28;
(Continued)

(56) References Cited

U.S. PATENT DOCUMENTS 4,500,780 A * 2/1985 Buan .................... G01D 5/3473
250/231.13
7,285,088 B2 * 10/2007 Miyake ................ A61B 1/0052
600/146
(Continued)

FOREIGN PATENT DOCUMENTS

JP S61-122619 A 6/1986
JP S63-093904 U 6/1988
(Continued)

OTHER PUBLICATIONS

Japanese Office Action dated Nov. 1, 2016 in related Japanese Patent Application No. 2013-226454.
(Continued)

*Primary Examiner* — Ryan J. Severson
(74) *Attorney, Agent, or Firm* — Scully, Scott, Murphy & Presser, P.C.

(57) ABSTRACT

A surgical instrument has a treatment section, a first pulling section and a second pulling section configured to transmit a pulling force to the treatment section, a power source configured to generate force for operating the treatment section, and a switching section having a first path configured to transmit the force from the power source to the first pulling member and a second path configured to transmit the force from the power source to the second pulling member and configured to switch the first path and the second path.

20 Claims, 13 Drawing Sheets

(51) Int. Cl.
   *A61B 1/00* (2006.01)
   *G02B 23/24* (2006.01)
   *A61B 1/005* (2006.01)
   *A61B 34/30* (2016.01)
   *A61B 34/37* (2016.01)
   *F16H 19/04* (2006.01)

(52) U.S. Cl.
   CPC ............ *A61B 1/0057* (2013.01); *A61B 34/30* (2016.02); *A61B 34/37* (2016.02); *F16H 19/04* (2013.01); *G02B 23/24* (2013.01); *A61B 17/29* (2013.01); *A61B 2034/305* (2016.02); *A61B 2034/715* (2016.02)

(58) Field of Classification Search
   CPC ................ A61B 17/2804; A61B 17/29; A61B 2017/00292; A61B 2017/003; A61B 2017/00318; A61B 2017/00323; A61B 2017/00327; A61B 2017/2901; A61B 2017/2902; A61B 2017/2908; A61B 2017/2927; A61B 2017/2932; A61B 2034/302; A61B 2034/305; A61B 2034/715; A61B 34/30; A61B 34/37; A61B 34/71; A61B 34/72
   See application file for complete search history.

(56) References Cited

U.S. PATENT DOCUMENTS

| | | | | |
|---|---|---|---|---|
| 7,540,867 B2* | 6/2009 | Jinno | .................... | A61B 34/70 414/7 |
| 8,277,443 B2* | 10/2012 | Jinno | .................... | B25J 9/104 606/1 |
| 8,333,780 B1* | 12/2012 | Pedros | .................... | A61B 17/29 600/37 |
| 8,382,659 B2* | 2/2013 | Ashida | .................... | A61B 1/00006 600/145 |
| 8,644,988 B2* | 2/2014 | Prisco | .................... | A61B 34/71 600/146 |
| 8,647,330 B2* | 2/2014 | Iida | .................... | A61B 34/71 606/1 |
| 8,795,324 B2* | 8/2014 | Kawai | .................... | A61B 17/29 606/205 |
| 9,101,379 B2* | 8/2015 | Au | .................... | A61B 19/2203 |
| 9,198,729 B2* | 12/2015 | Rogers | .................... | A61B 19/2203 |
| 9,259,274 B2* | 2/2016 | Prisco | .................... | B25J 9/1045 |
| 9,770,299 B2* | 9/2017 | Komuro | .................... | A61B 90/50 |
| 9,775,677 B2* | 10/2017 | Hyodo | .................... | A61B 34/71 |
| 2005/0054899 A1* | 3/2005 | Miyake | .................... | A61B 1/0052 600/152 |
| 2009/0031842 A1* | 2/2009 | Kawai | .................... | A61B 17/29 74/490.01 |
| 2009/0112230 A1* | 4/2009 | Jinno | .................... | B25J 9/104 606/130 |
| 2010/0082041 A1* | 4/2010 | Prisco | .................... | B25J 9/1045 606/130 |
| 2010/0241135 A1* | 9/2010 | Iida | .................... | A61B 34/71 606/130 |
| 2011/0009698 A1* | 1/2011 | Ashida | .................... | A61B 1/00006 600/118 |
| 2012/0123200 A1* | 5/2012 | Rogers | .................... | A61B 19/2203 600/104 |
| 2012/0123441 A1* | 5/2012 | Au | .................... | A61B 19/2203 606/130 |
| 2014/0107667 A1* | 4/2014 | Komuro | .................... | A61B 19/22 606/130 |
| 2014/0249545 A1* | 9/2014 | Hyodo | .................... | A61B 19/2203 606/130 |
| 2016/0038239 A1* | 2/2016 | Yamanaka | .................... | A61B 19/2203 606/130 |
| 2016/0051331 A1* | 2/2016 | Rogers | .................... | A61B 19/2203 606/130 |
| 2016/0166342 A1* | 6/2016 | Prisco | .................... | B25J 9/1045 606/130 |
| 2016/0206390 A1* | 7/2016 | Yoshii | .................... | F16H 19/0672 |
| 2016/0213438 A1* | 7/2016 | Jogasaki | .................... | A61B 1/0016 |
| 2017/0251902 A1* | 9/2017 | Jogasaki | .................... | A61B 1/00133 |
| 2017/0325905 A1* | 11/2017 | Jogasaki | .................... | A61B 34/74 |
| 2017/0333143 A1* | 11/2017 | Yoshii | .................... | A61B 34/30 |
| 2017/0340398 A1* | 11/2017 | Higuchi | .................... | A61B 34/37 |

FOREIGN PATENT DOCUMENTS

| | | |
|---|---|---|
| JP | H06-130307 A | 5/1994 |
| JP | H07-116104 A | 5/1995 |
| JP | H10-174686 A | 6/1998 |
| JP | 2004-350866 A | 12/2004 |
| JP | 2007-029167 A | 2/2007 |
| JP | 2009-225992 A | 10/2009 |
| JP | 2012-504016 A | 2/2012 |
| JP | 2013-103074 A | 5/2013 |
| WO | WO 2012/064528 A1 | 5/2012 |
| WO | 2014/123246 A1 | 8/2014 |

OTHER PUBLICATIONS

International Search Report dated Feb. 3, 2015 issued in PCT/JP2014/078901.
Extended Supplementary European Search Report dated Apr. 25, 2017 in European Patent Application No. 14 85 8559.9.

* cited by examiner

SURGICAL INSTRUMENT

This application is a continuation application based on PCT Patent Application No. PCT/JP2014/078901, filed Oct. 30, 2014, claiming priority based on Japanese Patent Application 2013-226454, filed Oct. 31, 2013, the content of which is incorporated herein by reference.

BACKGROUND OF THE INVENTION

Field of the Invention

The present invention relates to a surgical instrument including a medical endoscope.

Description of the Related Art

In the related art, a medical manipulator configured to support an operation is known.

For example, Japanese Unexamined Patent Application, First Publication No. 2007-029167 discloses an endoscope having a driving shaft body to which a driving force generated from a driving force-generating means is transmitted, a driven shaft body operated by the driving shaft body, and a curving manipulation wire fixed to the driven shaft body, and the endoscope being configured such that a curved section to which the curving manipulation wire is fixed receives a driving force and is curved by the driving force-generating means.

In the endoscope disclosed in Japanese Unexamined Patent Application, First Publication No. 2007-029167, the driven shaft body is a set of racks constituted by two racks connected to each other by a pinion, and one curving manipulation wire is fixed to one rack. As a result that a second rack pushes a second curving manipulation wire with the same amount that a first rack pulls a first curving manipulation wire when the first rack pulls the first curving manipulation wire, the two curving manipulation wires fixed to the set of racks advance and retract in opposite directions.

SUMMARY OF THE INVENTION

A surgical instrument according to a first aspect of the present invention includes a treatment section configured to treat a treatment target; a first pulling section configured to transmit a pulling force to the treatment section to operate the treatment section; a second pulling section configured to transmit a pulling force to the treatment section to operate the treatment section; a power source configured to generate force for operating the treatment section; and a switching section having a first path configured to transmit the force from the power source to the first pulling section and a second path configured to transmit the force from the power source to the second pulling section and the switching section being configured to switch the first path and the second path According to a second aspect of the present invention, in the surgical instrument according to the first aspect, the first pulling section may have a first pulling member that is flexible and connected to the treatment section, the second pulling section may have a second pulling member that is flexible and connected to the treatment section, and the switching section may have: a first engaging body to which the first pulling member is connected; and a second engaging body to which the second pulling member is connected.

According to a third aspect of the present invention, in the surgical instrument according to the first aspect, the first pulling section and the second pulling section may be a series of flexible linear members connected at proximal ends thereof.

According to a fourth aspect of the present invention, in the surgical instrument according to the second aspect, the switching section may have a tension-applying section configured to apply common tension to a first region in the first pulling member from a contact position of the first pulling member and the first engaging body to the treatment section, and a second region in the second pulling member from a contact position of the second pulling member and the second engaging body to the treatment section.

According to a fifth aspect of the present invention, in the surgical instrument according to the second aspect, the first engaging body may be a first rack section to which the first pulling member is fixed, the second engaging body may be a second rack section to which the second pulling member is fixed, and the switching section may have: a pinion configured to be capable of meshing with the first rack section and the second rack section; a moving section configured to move the pinion to switch between a first transmission state and a second transmission state, the first transmission state in which the first rack section is meshed with the pinion and the second rack section is spaced from the pinion, the second transmission state in which the second rack section is meshed with the pinion and the first rack section is spaced from the pinion; and a transmission section configured to transmit the force from the power source to the pinion.

According to a sixth aspect of the present invention, in the surgical instrument according to the fifth aspect, the first rack section may have: a first pulling rack to which the first pulling member is fixed; a first facing rack having teeth facing teeth of the first pulling rack and disposed parallel to the first pulling rack; a first gear configured to be meshed with both of the first pulling rack and the first facing rack so as to connect the first pulling rack and the first facing rack; and a first pressing rack configured to be capable of meshing with the pinion, and configured to be capable of advancing and retracting in a longitudinal direction of the first facing rack due to the pinion, and configured to press the first facing rack such that the first facing rack moves in the longitudinal direction of the first facing rack, and the second rack section may have: a second pulling rack to which the second pulling member is fixed; a second facing rack having teeth facing teeth of the second pulling rack and disposed parallel to the second pulling rack; a second gear configured to be meshed with both of the second pulling rack and the second facing rack so as to connect the second pulling rack and the second facing rack; and a second pressing rack configured to configured to be capable of meshing with the pinion, and configured to be be capable of advancing and retracting in a longitudinal direction of the second facing rack due to the pinion, and configured to press the second facing rack such that the second facing rack moves in the longitudinal direction of the second facing rack.

According to a seventh aspect of the present invention, in the surgical instrument according to the fourth aspect, the first engaging body may be a first rack section to which the first pulling member is fixed, the second engaging body may be a second rack section to which the second pulling member is fixed, the switching section may have: a pinion configured to be capable of meshing with the first rack section and the second rack section; a moving section configured to move the pinion to switch between a first transmission state and a second transmission state, the first transmission state in which the pinion is meshed with the first rack section and the pinion is spaced from the second rack section, and the second transmission state in which the pinion is meshed with the second rack section and the pinion is spaced from the first rack section; and a transmission section configured to transmit the force from the power source to the pinion, the first rack section may have: a first pulling rack to which the first pulling member is fixed; a first facing rack having teeth facing teeth of the first pulling rack and disposed parallel to the first pulling rack; a first gear configured to mesh with both of the first pulling rack and the first facing rack so as to connect the first pulling rack and the first facing rack; and a first pressing rack configured to be capable of meshing with the pinion and configured to be capable of advancing and retracting in a longitudinal direction of the first facing rack due to the pinion, and configured to press the first facing rack such that the first facing rack moves in a longitudinal direction of the first facing rack, the second rack section may have: a second pulling rack to which the second pulling member is fixed; a second facing rack having teeth facing teeth of the second pulling rack and disposed parallel to the second pulling rack; a second gear configured to mesh both of the second pulling rack and the second facing rack so as to connect the second pulling rack and the second facing rack; and a second pressing rack configured to be capable of meshing with the pinion and configured to be capable of advancing and retracting in a longitudinal direction of the second facing rack due to the pinion, and configured to press the second facing rack such that the second facing rack moves in the longitudinal direction of the second facing rack, and the tension-applying section connects the first facing rack and the second facing rack.

According to an eighth aspect of the present invention, in the surgical instrument according to the second or fourth aspect, the first engaging body may be a first internal gear having an outer circumferential surface with which the first pulling member is frictionally engaged, the second engaging body may be a second internal gear having an outer circumferential surface with which the second pulling member is frictionally engaged, and the switching section may have: a holding section configured to hold the first internal gear and the second internal gear such that the first internal gear and the second internal gear are independently rotatable about the same rotational center; a pinion configured to be capable of meshing with the first internal gear and the second internal gear; a moving section configured to move the pinion between a first transmission state and a second transmission state, the first transmission state in which the pinion is meshed with the first internal gear and the pinion is separated from the second internal gear, the second transmission state in which the pinion is meshed with the second internal gear and the pinion is separated from the first internal gear; and a transmission section configured to transmit the force from the power source to the pinion.

According to a ninth aspect of the present invention, in the surgical instrument according to the fifth or eighth aspect, the moving section may have a third transmission state in which the pinion is simultaneously meshed with both of the first engaging body and the second engaging body, and the first transmission state and the second transmission state are switched to each other via the third transmission state.

DETAILED DESCRIPTION OF THE PREFERRED EMBODIMENTS

First Embodiment

A first embodiment of a surgical instrument 1 of the present invention will be described.

The surgical instrument 1 according to the embodiment is incorporated into a medical manipulator system configured to perform medical treatment.

First, a configuration of the medical manipulator system into which the surgical instrument 1 according to the embodiment is incorporated will be described.

Figure 1:
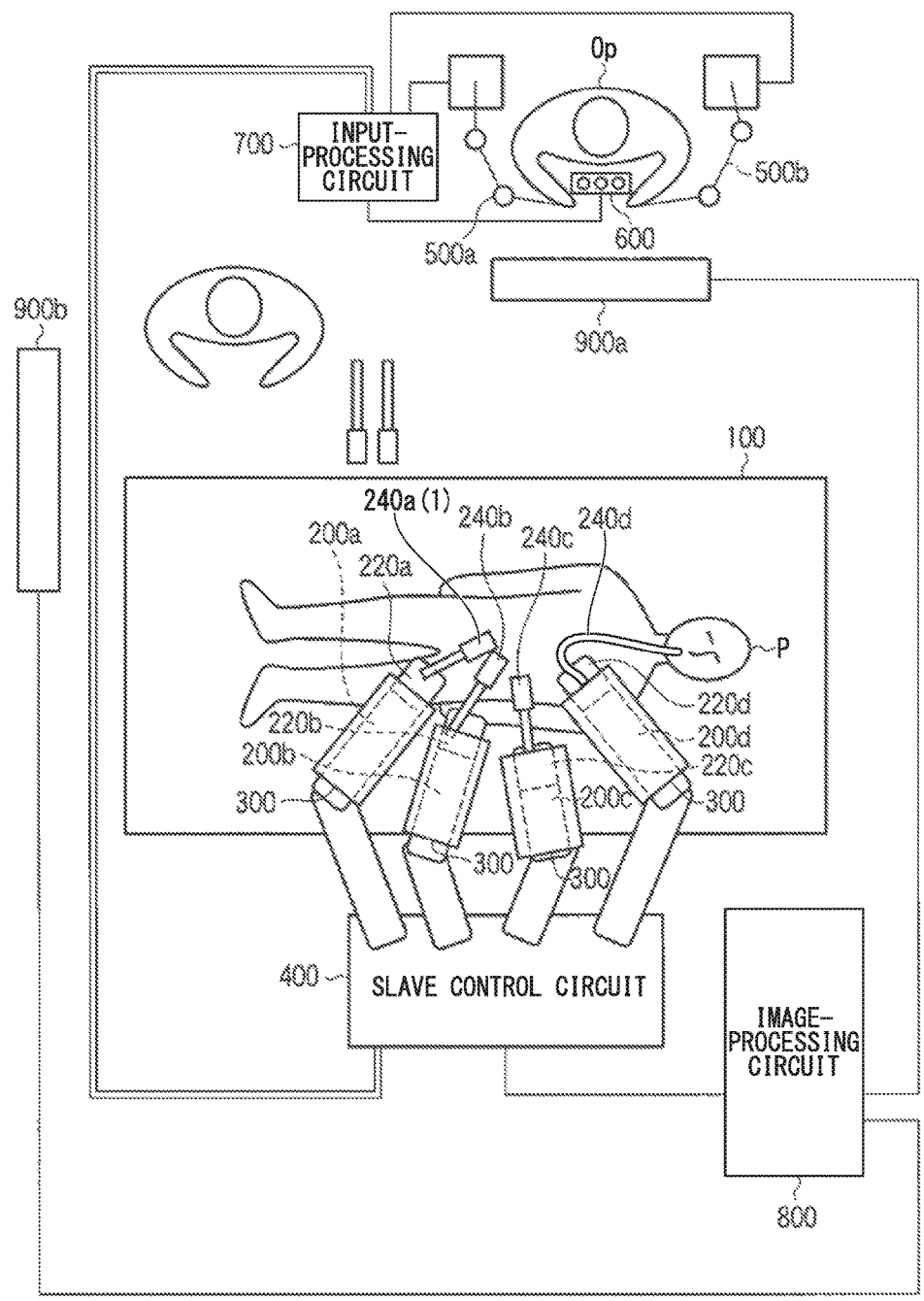
FIG. 1 is a schematic diagram showing an example of a medical manipulator system into which a surgical instrument according to a first embodiment of the present invention is incorporated.

FIG. 1 is a schematic diagram showing an example of a configuration of the medical manipulator to which the surgical instrument according to the embodiment is applied.

In FIG. 1, an example of a master-slave type medical manipulator system is shown.

The master-slave type medical manipulator system is a system having two arms constituted by a master arm and a slave arm and configured to remotely control the slave arm by following an operation of the master arm. In the embodiment, the surgical instrument 1 can be mounted on the slave arm.

The medical manipulator system shown in FIG. 1 has a surgical table 100, slave arms 200a, 200b, 200c and 200d, a slave control circuit 400, master arms 500a and 500b, a manipulation section 600, an input-processing circuit 700, an image-processing circuit 800, a display 900a for an operator and a display 900b for an assistant.

In the following description, for describing concisely, reference numerals "Xa, Xb, . . . , Xz" in alphabetical order may be represented as "Xa to Xz." For example, "the slave arms 200a, 200b, 200c and 200d" may be represented as "the slave arms 200a to 200d."

The surgical table 100 is a table on which a patient P who is a subject of observation or treatment lies. The plurality of slave arms 200a to 200d are installed in the vicinity of the surgical table 100. Further, the slave arms 200a to 200d may be installed on the surgical table 100.

Each slave arm 200a to 200d is configured to have a plurality of multi-degree-of-freedom joint. The slave arms 200a to 200d adjust positions of the surgical instrument 1, surgical instruments 240a to 240d, or the like, mounted on a distal end side (a side toward a body cavity of the patient P) of the slave arms 200a to 200d with respect to the patient P lying on the surgical table 100 by curving the multi-degree-of-freedom joint. The multi-degree-of-freedom joint are individually driven by power units (not shown). The power unit may be, for example, a motor having a servo mechanism including an incremental encoder, a speed reducer, or the like. The operation control is performed by the slave control circuit 400.

The surgical instrument 1 or the other surgical instruments 240a to 240d may be hard or flexible. That is, the surgical instrument 1 or the surgical instruments 240a to 240d may be employed by appropriately selecting a surgical instrument configured to operate an effector that performs treatment on a living body by pushing or pulling a rigid rod, or a surgical instrument configured to operate an effector that performs treatment on a living body by pulling a flexible wire. Further, even when the surgical instrument 1 or the other surgical instruments 240a to 240d are rigid, the surgical instrument may have a configuration for moving the effector by pulling the flexible wire. In the embodiment, the surgical instrument 1 has a configuration for transmitting a driving force for operating the effector to the effector through the flexible wire.

FIG. 1 shows an example in which the surgical instrument 1 and the other surgical instruments 240a to 240c are rigid and the surgical instrument 240d is flexible. The flexible surgical instrument 240d is introduced into the body via the alimentary canal or the like from a natural opening of the patient, for example, the mouth or the like.

The slave control circuit 400 is configured to have, for example, a CPU, a memory, or the like. The slave control circuit 400 stores a predetermined program to control the slave arms 200a to 200d, and controls operations of the slave arms 200a to 200d, the surgical instrument 1 or the other surgical instruments 240a to 240d according to a control signal from the input-processing circuit 700. That is, the slave control circuit 400 specifies the slave arm (or the surgical instrument 1) which is the manipulation target of the master arm being manipulated by an operator Op and calculates a driving amount required for causing the specified slave arm or the like to move to correspond to a manipulation amount of the master arm by the operator Op based on the control signal from the input-processing circuit 700.

Then, the slave control circuit 400 controls an operation of the slave arm or the like of the manipulation target of the master arm according to the calculated driving amount. Here, the slave control circuit 400 inputs a driving signal and controls a magnitude or a polarity of the driving signal such that the driving amount of the slave arm of the manipulation target becomes equal to a desired driving amount depend on a detection signal being input from a position detector of a power unit according to the operation of the corresponding slave arm.

The master arms 500a and 500b are constituted by a plurality of link mechanisms. For example, a position detector such as an incremental encoder or the like is installed at each of the links that constitute the link mechanism. As the operation of each of the links is detected by the position detector, the manipulation amounts of the master arms 500a and 500b are detected in the input-processing circuit 700.

The medical manipulator system shown in FIG. 1 is configured to manipulate four slave arms by using the two master arms 500a and 500b, and appropriately switches the slave arms of the manipulation target of the master arm. Such switching is performed by, for example, manipulation of the manipulation section 600 of the operator Op. Of course, when the number of master arms is equal to the number of slave arms to correspond to the manipulation targets one to one, it is unnecessary such switching.

The manipulation section 600 has various kinds of manipulation members such as switching buttons configured to switch the slave arms of the manipulation targets of the master arms 500a and 500b, a scaling change switch configured to change an operation ratio of the master and the slave, a foot switch configured to stop the system suddenly, or the like. When any one of the manipulation members that constitute the manipulation section 600 is manipulated by the operator Op, the manipulation signal in accordance with the manipulation of the corresponding manipulation member is input to the input-processing circuit 700 from the manipulation section 600.

The input-processing circuit 700 analyzes the manipulation signals from the master arms 500a and 500b and the manipulation signal from the manipulation section 600, and generates a control signal for controlling the medical manipulator system according to the analysis result of the manipulation signal to input the control signal to the slave control circuit 400.

The image-processing circuit 800 performs various kinds of image processing to display an image signal input from the slave control circuit 400, and generates image data for display in the display 900a for an operator and the display 900b for an assistant. The display 900a for an operator and the display 900b for an assistant are constituted by, for example, a liquid crystal display, and display images based on the image data generated in the image-processing circuit 800 according to the image signal acquired by an observation instrument.

In the medical manipulator system having the above-mentioned configuration, when the operator Op manipulates the master arms 500a and 500b, the surgical instrument 1 or the other surgical instruments 240a to 240d to which the corresponding slave arm and the corresponding slave arm are attached perform to correspond to movement of the master arms 500a and 500b. Accordingly, a desired procedure can be performed on the patient P.

In FIG. 1, reference numerals 220a, 220b, 220c and 220d designate adaptors of transmitting power for an operation, which are disposed between the slave arms 200a, 200b, 200c and 200d and the surgical instruments 240a, 240b, 240c and 240d and connect the slave arms 200a, 200b, 200c and 200d and the surgical instruments 240a, 240b, 240c and 240d.

Reference numeral 300 is a drape configured to partition an area (a clean area) in which sterilization processing is performed and an area (an unclean area) in which sterilization processing is not performed in the medical manipulator system according to the embodiment.

Next, the surgical instrument 1 incorporated into the medical manipulator system of the embodiment will be described. Here, in a state in which the surgical instrument 1 is incorporated into the medical manipulator system, a side of the surgical instrument 1 directed toward the body cavity of the patient P is called a distal side of the surgical instrument 1, and a connection portion side with respect to the medical manipulator system at a side apart from the patient P is a proximal side of the surgical tool 1 is called a proximal side of the surgical instrument 1 in the description of the surgical instrument 1 according to the embodiment.

Figure 2:
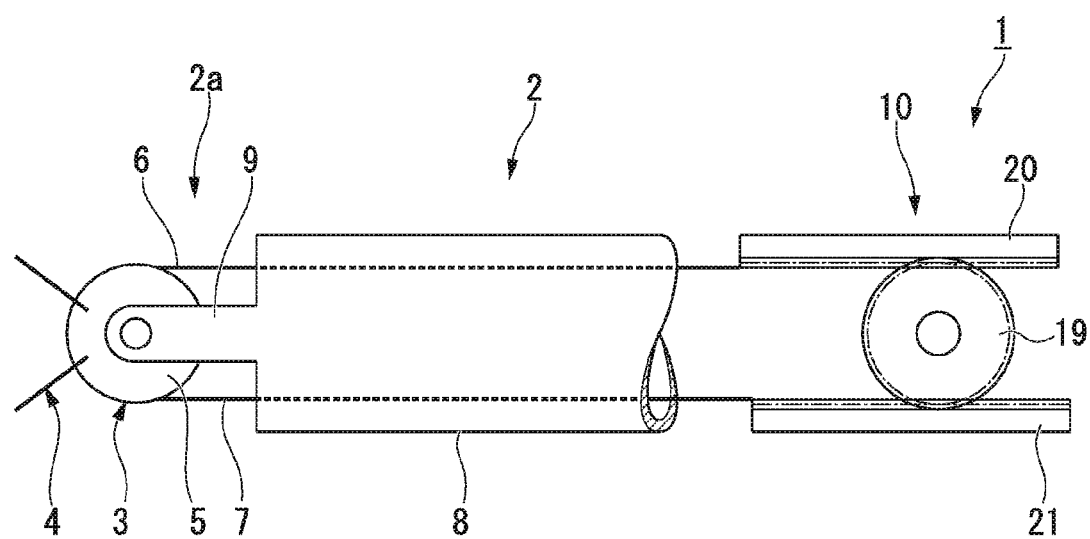
FIG. 2 is a schematic diagram showing the entire surgical instrument according to the first embodiment of the present invention.
Figure 3:
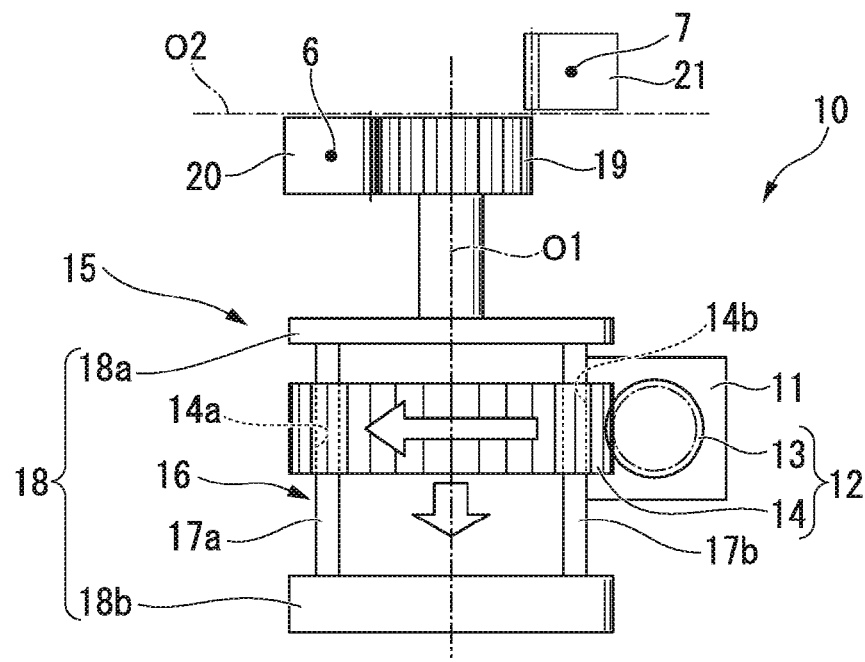
FIG. 3 is a schematic diagram showing a configuration of a driving section of the surgical instrument according to the first embodiment of the present invention.
Figure 4:
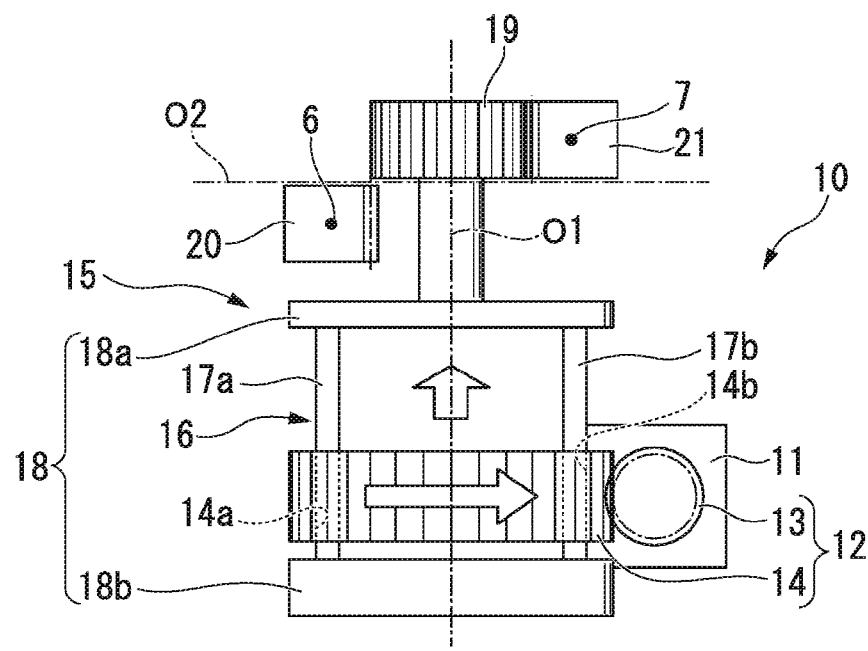
FIG. 4 is a schematic diagram showing the configuration of the driving section of the surgical instrument according to the first embodiment of the present invention.

FIG. 2 is a schematic diagram showing the entire surgical instrument 1. FIGS. 3 and 4 are schematic diagrams showing a configuration of a driving section of the surgical instrument 1.

The surgical instrument 1 according to the embodiment is attached to the slave arms 200a to 200d shown in FIG. 1. The surgical instrument 1 is operated corresponding to the manipulation which is input to the master arms 500a and 500b.

As shown in FIG. 2, the surgical instrument 1 has an insertion section 2 and a driving section 10. The insertion section 2 has a distal end section 2a inserted into the body. The driving section 10 is attached to a proximal end of the insertion section 2. The insertion section 2 has a treatment section 3 and a pipe section 8. The treatment section 3 is installed to treat a treatment target. The treatment section 3 is connected to a distal end of the pipe section 8.

The surgical instrument 1 may function as an endoscope. That is, the surgical instrument 1 may be an endoscope. When the surgical instrument 1 is the endoscope, the surgical instrument 1 includes an observation means configured to observe (treat) the inside of the body as a treatment section. In addition, the surgical instrument 1 configured as the endoscope may further include an illumination means configured to radiate illumination light to the observation target or the treatment target. The surgical instrument 1 may have a function such that a means for observing the inside of the body is included but a means for performing surgical treatment is not include.

The treatment section 3 is installed at a distal end section of the insertion section 2. The treatment section 3 may include a known configuration corresponding to treatment content of the treatment target. For example, a forceps, a knife, a marking device, a suture instrument, and so on may be provided as examples of the treatment section 3. In the embodiment, the treatment section 3 is a grasping forceps 4 configured to grasp the treatment target.

The grasping forceps 4 can be opened and closed by a known opening/closing mechanism. The grasping forceps 4 can swing by an operation rotating around a predetermined pivotal shaft 5. Further, as another mechanisms configured to swing the grasping forceps 4, a mechanism in which a plurality of bending pieces that are connected to be bendable are installed at the distal end of the insertion section 2 and it can be deformed in a curved shape as a whole by bending the bending pieces are bent is known.

Distal portions of a first pulling member 6 (a first pulling section) that is flexible and a second pulling member 7 (a second pulling section) that is flexible are wound on the outer circumferential surface of the pivotal shaft 5. The distal ends of the first pulling member 6 and the second pulling member 7 are connected to the pivotal shaft 5.

When the swing mechanism in which the bending pieces are used is employed, the distal ends of the first pulling member 6 and the second pulling member 7 are fixed to the bending pieces disposed at the most distal end among the plurality of bending pieces or a structure (for example, the proximal end of the treatment section 3 or the like) which is positioned closer to the distal end than the bending piece disposed at the most distal end.

The first pulling member 6 and the second pulling member 7 have flexibility so as to be capable of curving to follow the outer circumferential surface of the pivotal shaft 5. For example, the first pulling member 6 and the second pulling member 7 are formed of a material such as stainless steel (for example, SUS304) in a wire shape.

In the embodiment, the first pulling member 6 and the second pulling member 7 are wound on the outer circumferential surface of the pivotal shaft 5 and pulled to be swung. For this reason, a material of the first pulling member 6 and the second pulling member 7 may be likely to bend but may not easily expand or contract. However, in general, an easily bendable material is likely to expand or contract, and a material that does not easily expand or contract does not easily bend either. In the embodiment, the material of the first pulling member 6 and the second pulling member 7 is selected in consideration of a balance between ease of bending and elasticity of the first pulling member 6 and the second pulling member 7.

The pipe section 8 is a hollow member and provided with a holding section 9 at a distal end thereof. The holding section 9 pivotally holds the pivotal shaft 5. The first pulling member 6 and the second pulling member 7 are inserted through the pipe section 8 to freely advance and retract. In the embodiment, the pipe section 8 is rigid and formed in a tubular shape. The pipe section 8 may have flexibility.

As shown in FIG. 3, the driving section 10 has a power source 11, a transmission section 12 and a switching section 15. The driving source 11 generates force for swinging the treatment section 3 shown in FIG. 2. The transmission section 12 is connected to the power source 11. The switching section 15 is connected to the transmission section 12.

The power source 11 receives a driving signal generated based on the manipulation input using the master arms 500a and 500b shown in FIG. 1 and generates force corresponding to the manipulation input on the master arms 500a and 500b. A configuration of the power source 11 is not particularly limited. In the embodiment, for example, the power source 11 is a servo motor.

If there are two of the power sources 11, the problems that two pulled curving manipulation wires which move in opposite directions may occur stretch, slack and bend can be solved even when the configuration like the embodiment is not provided. However, in this case, power sources for clutch functions and power sources for operating clutch mechanisms should be provided at the two power sources, therefore, four power sources are required for one pivotal shaft 5, leading to an increase in size of the apparatus. For this reason, provision of a power source as an auxiliary machine in addition to the power source 11 is not realistic or practical. A driving means installed at a manipulation section of an endoscope in order to bend a distal end portion of an insertion section of the endoscope inserted into the body is known to be manipulated manually. However, a configuration of a knob or the like for performing manipulation input should be installed at the manipulation section of each of the power sources when a plurality of power sources that are operated by manual manipulation are provided. In addition, a configuration of performing the manipulation input is further added when an auxiliary machine is further needed for the power source in the driving means according to the manual manipulation. That is, since at least two manipulation sections are needed for the one pivotal shaft 5 and this is extremely hard to manipulate, the case of the manual manipulation is also considered impractical.

The transmission section 12 has a worm gear 13 and a worm wheel 14. The worm gear 13 is fixed to an output shaft of a servo motor as the power source 11. The worm wheel 14 is configured to be meshed with the worm gear 13.

The worm gear 13 and the worm wheel 14 are always meshed with each other. The worm wheel 14 is held by a holding means (not shown) such that a rotational center O1 of the worm wheel 14 passes through a gap between a first pulling rack 20 and a second pulling rack 21 (to be described below). Two through-holes 14a and 14b are formed in the worm wheel 14 so as to extend in a rotational center axial direction of the worm wheel 14. Two connecting shafts 17a and 17b (to be described below) are inserted through the two through-holes 14a and 14b so as to freely advance and retract.

Each of centers of the two through-holes 14a and 14b are disposed to be spaced an equal distance from a rotational center of the worm wheel 14 with the rotational center interposed therebetween, and disposed parallel to a straight line passing the rotational center of the worm wheel 14 when seen from a direction in which the rotational center of the worm wheel 14 extends. Each of the centers of the two through-holes 14a and 14b may not be disposed an equal distance from the rotational center of the worm wheel 14 with the rotational center interposed therebetween as long as the centers correspond to the positions of the connecting shafts 17a and 17b.

The switching section 15 has a moving section 16, a pinion 19, a first engaging body and a second engaging body. The moving section 16 is capable of advancing and retracting in a direction in which the rotational center of the worm wheel 14 extends and the moving section 16 is integrally rotatable with the worm wheel 14. The pinion 19 is fixed to the moving section 16 and is coaxial with the rotational center of the worm wheel 14. The first engaging body is fixed to the first pulling member 6. The second engaging body is fixed to the second pulling member 7.

The moving section 16 has two connecting shafts 17a and 17b, and end section members 18 (a first end section member 18a and a second end section member 18b). The connecting shafts 17a and 17b pass through each of the through-holes 14a and 14b of the worm wheel 14 and extend parallel to the rotational center of the worm wheel 14. The end section members 18 are installed at both ends of the connecting shafts 17a and 17b so as to connect the connecting shafts 17a and 17b.

The two connecting shafts 17a and 17b are disposed to be spaced an equal distance from the rotational center of the worm wheel 14 with the rotational center interposed therebetween, and disposed parallel to the straight line passing the rotational center of the worm wheel 14 when seen from the direction in which the rotational center of the worm wheel 14 extends.

In consideration of design and assembly, the connecting shafts 17a and 17b may be preferably inserted into the through-holes 14a and 14b disposed to be spaced an equal distance from the rotational center of the worm wheel 14 with the rotational center interposed therebetween.

Instead of installation of the connecting shafts 17a and 17b, another structure configured to connect the first end section member 18a and the second end section member 18b may be employed. For example, instead of the connecting shafts 17a and 17b, the first end section member 18a and the second end section member 18b may be connected by one connecting shaft. Cross-sectional shapes of the connecting shafts 17a and 17b in a cross-section perpendicular to the rotational center of the worm wheel 14 are not particularly limited.

The pinion 19 is fixed to any one (in the embodiment, the first end section member 18a) of the first end section member 18a and the second end section member 18b. An actuator configured to move the moving section 16 in the rotational center axial direction of the worm wheel 14 is connected to the other member (in the embodiment, the second end section member 18b) of the first end section member 18a and the second end section member 18b.

A configuration of the second end section member 18b and the actuator connected thereto is not particularly limited as long as the second end section member 18b is rotatable about the rotational center of the worm wheel 14 and the second end section member 18b is movable to advance and retract in the rotational center axial direction of the worm wheel 14.

Figure 5:
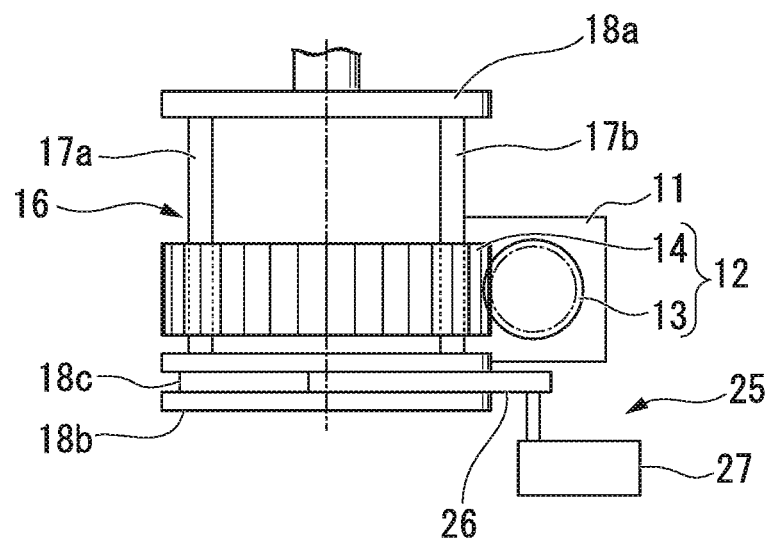
FIG. 5 is a schematic side view showing an example of the configuration of the driving section according to the first embodiment of the present invention.

FIG. 5 is a schematic side view showing an example of a configuration in which the second end section member 18b is rotatable about the rotational center of the worm wheel 14 and the second end section member 18b is capable of advancing and retracting in the rotational center axial direction of the worm wheel 14. In addition, FIG. 6 is a bottom view of FIG. 5.

As an example of the configuration of the second end section member 18b and an actuator 25, as shown in FIG. 5, the second end section member 18b has a disk shape and has a groove section 18c which has a circular shape with the rotational center of the worm wheel 14 as a center on an outer circumferential surface of the disk shape, and the actuator 25 has a U-shaped member 26 and a motor 27. The U-shaped member 26 is partially inserted into the groove section 18c of the second end section member 18b. The motor 27 moves the U-shaped member 26 to advance and retract in the rotational center axial direction of the worm wheel 14.

Figure 6:
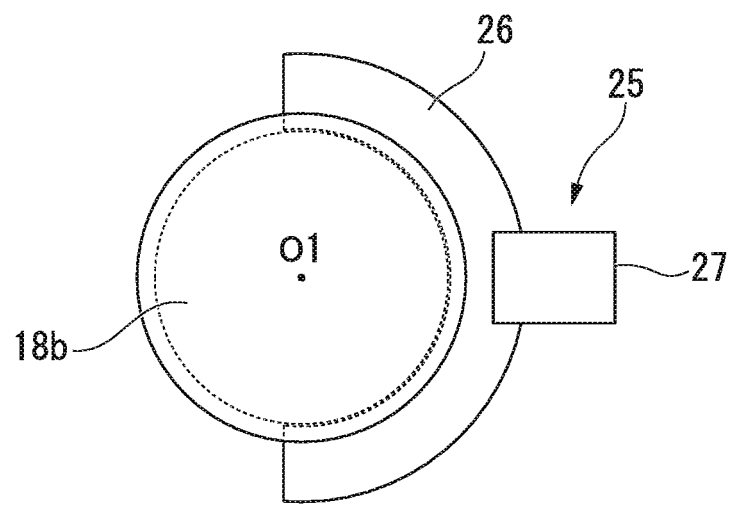
FIG. 6 is a bottom view of the driving section shown in FIG. 5.

As shown in FIGS. 5 and 6, the U-shaped member 26 has a shape following the outer surface of the bottom portion of the groove in the groove section 18c (a surface of the groove which is a surface of a columnar shape about the rotational center of the worm wheel 14 as a center). When the U-shaped member 26 is moved to advance and retract in the rotational center axial direction of the worm wheel 14 by the motor 27, the U-shaped member 26 is hooked to the groove section 18c to linearly move the second end section member 18b in the rotational center axial direction of the worm wheel 14. At this time, the U-shaped member 26 does not restrict rotation of the second end section member 18b about the rotational center of the worm wheel 14.

The actuator 25 may further include a guide configured to allow the U-shaped member 26 to move in the rotational center axial direction of the worm wheel 14 and restrict deviation of the U-shaped member 26 in a direction crossing the rotational center axial direction of the worm wheel 14.

The same groove section as the groove section 18c is formed in the first end section member 18a, and instead of the U-shaped member 26 or in addition to the U-shaped member 26, a U-shaped member inserted into the groove section of the first end section member 18a may be provided. In this case, the U-shaped member inserted into the groove section of the first end section member 18a may be moved by the motor 27.

Figure 16:
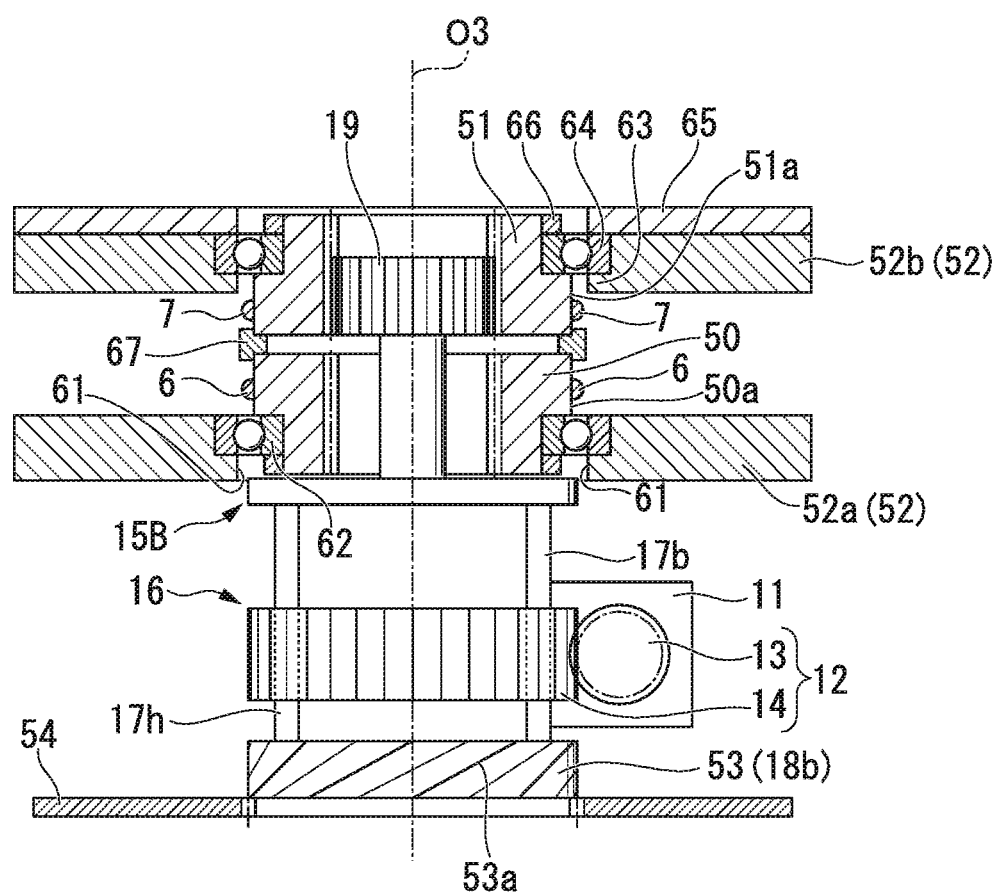
FIG. 16 is a schematic diagram showing the driving section according to the third embodiment of the present invention.

Another example of the configuration of the second end section member 18b and the actuator is a configuration in which a plurality of inclined convex sections are formed on the outer circumferential surface of the second end section member 18b and a support hole section is formed in a housing (not shown) of the driving section 10 (for example, see FIG. 16). The plurality of inclined convex sections forms a spiral shape about the rotational center of the worm wheel 14. That is, a plurality of inclined convex sections inclined with respect to the rotational center axis of the worm wheel 14 is formed on the outer circumferential surface of the second end section member 18b. The support hole section is a hole formed with a concavo-convex shape formed to engage with the inclined convex section. The inclined convex section and the support hole section are engaged with each other.

As still another example of the configuration of the second end section member 18b and the actuator, the second end section member 18b is formed in a disk shape having a thickness in the rotational center axial direction of the worm wheel 14, and the actuator has a connecting section slidably engaged with both end surfaces in a thickness direction of the second end section member 18b and a motor configured to move the connecting section to advance and retract in the rotational center axial direction of the worm wheel 14.

The pinion 19 is fixed to the first end section member 18a of the moving section 16. In addition, in the embodiment, the pinion 19 is a spur gear. A tapered portion to connect smoothly with a first engaging body (the first pulling rack 20) and a second engaging body (the second pulling rack 21) (to be described below) may be formed at the teeth formed on the pinion 19. The pinion 19 and the worm wheel 14 are configured to rotate about the same rotational center O1.

The first engaging body according to the embodiment is the first pulling rack 20 (a first rack section) to which the first pulling member 6 is fixed. The first pulling rack 20 is a rod-shaped member having teeth formed in a longitudinal direction thereof in parallel and configured to mesh with the teeth of the pinion 19. A proximal end of the first pulling member 6 is fixed to a distal end of the first pulling rack 20.

The second engaging body according to the embodiment is the second pulling rack 21 (a second rack section) to which the second pulling member 7 is fixed. The second pulling rack 21 is a rod-shaped member having teeth formed in a longitudinal direction of the second pulling rack 21 in parallel and configured to mesh with the teeth of the pinion 19. A proximal end of the second pulling member 7 is fixed to a distal end of the second pulling rack 21.

The first pulling rack 20 and the second pulling rack 21 extend parallel to each other. The teeth of the first pulling rack 20 and the second pulling rack 21 are formed to face each other. The teeth of the pinion 19 are appropriately meshed with the teeth of the first pulling rack 20 and the teeth of the second pulling rack 21. In the embodiment, the first pulling rack 20 and the second pulling rack 21 are disposed to be deviated from each other in an axial direction of the rotational center O1 of the pinion 19, and the second pulling rack 21 is spaced from the first pulling rack 20 in a direction O2 perpendicular to the axial direction of the rotational center O1 of the pinion 19 and perpendicular to a longitudinal direction of the first pulling rack 20. A distance between the first pulling rack 20 and the second pulling rack 21 in the direction O2 is substantially equal to a diameter of the pinion 19.

The pinion 19 is exclusively connected to each of the first pulling rack 20 and the second pulling rack 21. That is, the pinion 19 can be moved by the moving section 16 to advance and retract in a linear direction between a position at which the pinion 19 and the first pulling rack 20 are meshed with each other and a position at which the pinion 19 and the second pulling rack 21 are meshed with each other in the axial direction of the rotational center O1 of the pinion 19.

A state in which the pinion 19 and the first pulling rack 20 are meshed with each other as shown in FIG. 3 is a state in which power can be transmitted from the pinion 19 to the first pulling rack 20 (a first transmission state). A state in which the pinion 19 and the second pulling rack 21 are meshed with each other as shown in FIG. 4 is a state in which power can be transmitted from the pinion 19 to the second pulling rack 21 (a second transmission state).

For this reason, the switching section 15 of the embodiment has a first path configured to transmit force from the power source 11 to the first pulling member 6, and a second path configured to transmit force from the power source 11 to the second pulling member 7. The switching section 15 exclusively switches the first path and the second path by moving the pinion 19 in the axial direction of the rotational center O1 of the pinion 19. That is, as the result of that the moving section 16 moves the pinion 19 to switch between the first transmission state and the second transmission state, the switching section 15 exclusively switches and transmits the force generated by the power source 11 to the first pulling member 6 or the second pulling member 7.

In the embodiment, while the example in which the first path and the second path are exclusively switched has been described, the first path and the second path are not limited to such an exclusive switching configuration. That is, there may be a state in which the pinion 19 is meshed with both of the first pulling rack 20 and the second pulling rack 21 (a third transmission state). In a state in which the pinion 19 is meshed with both of the first pulling rack 20 and the second pulling rack 21, for example, when the pinion 19 moves from the first pulling rack 20 to the second pulling rack 21, the pinion 19 is also meshed with the second pulling rack 21 while being meshed with the first pulling rack 20, and when the pinion 19 moves from the second pulling rack 21 to the first pulling rack 20, the pinion 19 is also meshed with the first pulling rack 20 while being meshed with the second pulling rack 21. For this reason, when switching between the first transmission state and the second transmission state is performed through the third transmission state, unintended transmission of the force to the treatment section 3 due to abrupt switching between the first transmission state and the second transmission state is prevented.

Figure 7:
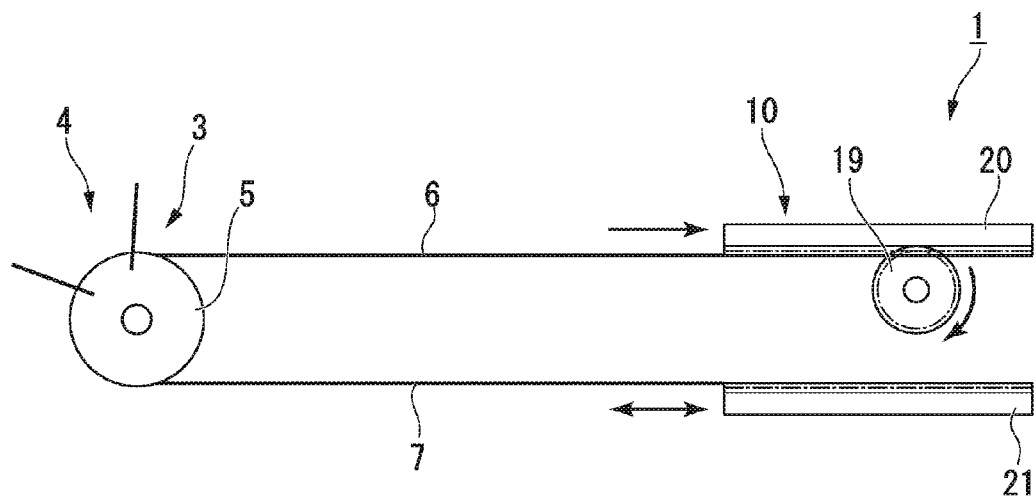
FIG. 7 is a view describing an action of the surgical instrument according to the first embodiment of the present invention.
Figure 8:
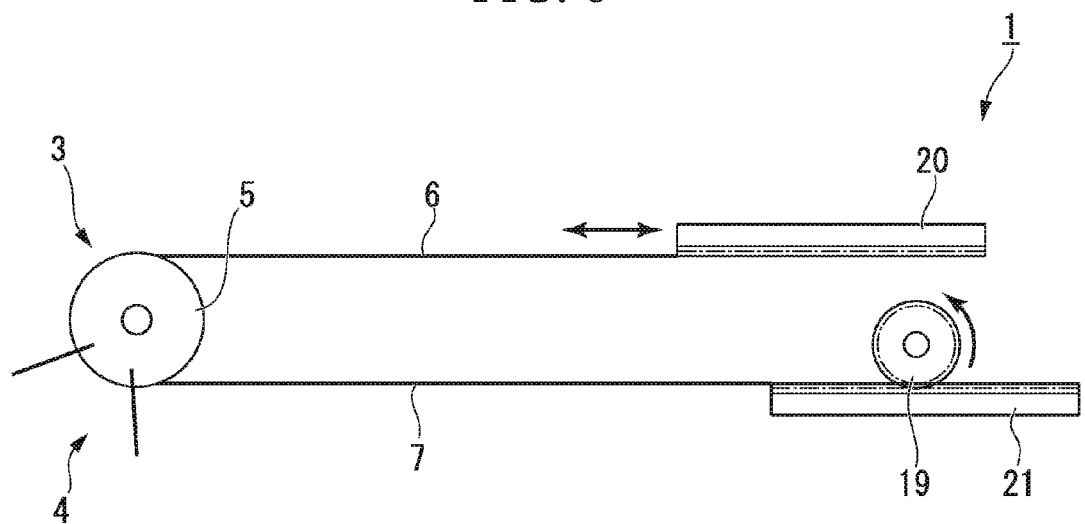
FIG. 8 is a view describing an action of the surgical instrument according to the first embodiment of the present invention.

Next, an action of the surgical instrument 1 according to the embodiment will be described. FIGS. 7 and 8 are views describing an action of the surgical instrument 1.

The surgical instrument 1 according to the embodiment is fixed to the slave arm, and the power source 11 of the driving section 10 moves in accordance with the manipulation input with respect to the master arm. When the first pulling member 6 in the surgical instrument 1 is pulled, before the power source 11 configured to rotate the worm wheel 14 of the moving section 16 is operated, the actuator (for example, the actuator 25 or the like shown in FIG. 5) configured to move the second end section member 18b of the moving section 16 is operated. That is, first, the actuator (not shown) configured to move the second end section member 18*b* moves the pinion 19 in the rotational center axial direction of the pinion 19 to a position at which the teeth of the pinion 19 are meshed with the teeth of the first pulling rack 20 (see FIG. 3). After that, as the power source 11 configured to rotate the worm wheel 14 of the moving section 16 is operated, while the power is transmitted from the pinion 19 to the first pulling rack 20, the power is not transmitted from the pinion 19 to the second pulling rack 21 (the first transmission state).

In addition, when the third transmission state is interposed therebetween, movement of the pinion 19 in the rotational center axial direction of the worm wheel 14 occurs during rotation of the pinion 19.

In the embodiment, since the first pulling member 6 has a flexible wire shape, in order to transmit the power to the treatment section 3 using the first pulling member 6, a force of pulling the first pulling member 6 is used. As a reason for this, a force of pressing the first pulling member 6 in the longitudinal direction may deform to bend and move the first pulling member 6 to an unintended position. In the embodiment, the force of pressing the first pulling member 6 toward the treatment section 3 is not actively used for transmission of the energy for operating the treatment section 3.

FIGS. 7 and 8 are schematic diagrams in which it can be easily seen which of the first pulling rack 20 and the second pulling rack 21 is meshed with the pinion 19, which differs when the first pulling rack 20 and the second pulling rack 21 are actually seen in the axial direction of the rotational center O1 of the pinion 19. That is, when the pinion 19 is meshed with any one of the first pulling rack 20 and the second pulling rack 21, the pinion 19 actually appears to come in contact with both of the first pulling rack 20 and the second pulling rack 21 when seen in the axial direction of the rotational center O1 of the pinion 19. However, FIGS. 7 and 8 schematically show that one of the first pulling rack 20 and the second pulling rack 21 that is not meshed with the pinion 19 is spaced from the pinion 19.

Here, as shown in FIG. 7, in a state in which the pinion 19 and the first pulling rack 20 are meshed with each other, if the pinion 19 and the second pulling rack 21 are meshed with each other, an operation in which the second pulling rack 21 presses the second pulling member 7 simultaneously with the operation in which the first pulling rack 20 pulls the first pulling member 6. In the embodiment, in a state in which the pinion 19 and the first pulling rack 20 are meshed with each other, the second pulling rack 21 is spaced from the pinion 19 and the second pulling rack 21 does not press the second pulling member 7. For this reason, it is possible to prevent the second pulling member 7 from deforming or unintentionally moving upon pulling of the first pulling member 6.

When the force is transmitted to the treatment section 3 from the first pulling member 6, the pulling force of the first pulling member 6 may be transmitted to the second pulling member 7 via the treatment section 3. In the embodiment, since the second pulling rack 21 and the pinion 19 are spaced from each other upon pulling of the first pulling member 6, when the pulling force of the first pulling member 6 is transmitted to the second pulling member 7 via the treatment section 3, the second pulling member 7 moves the second pulling rack 21 in the longitudinal direction of the second pulling rack 21 without receiving restriction from the pinion 19. Accordingly, the second pulling member 7 is configured hardly slacken.

On the other hand, when the second pulling member 7 is pulled in the surgical instrument 1, before the power source 11 configured to rotate the worm wheel 14 of the moving section 16 is operated, the actuator (the actuator 25 or the like shown in FIG. 5) configured to move the second end section member 18*b* of the moving section 16 is operated. That is, first, the actuator configured to move the second end section member 18*b* moves the pinion 19 in the axial direction of the rotational center O1 to the position at which the teeth of the pinion 19 are meshed with the teeth of the second pulling rack 21 (see FIG. 4). After that, due to an operation of the power source 11 configured to rotate the worm wheel 14 of the moving section 16 is operated, while the power is transmitted from the pinion 19 to the second pulling rack 21, the power is not transmitted from the pinion 19 to the first pulling rack 20 (the second transmission state).

The operation of the power source 11 and the operation of the actuator may be simultaneously performed. In this case, the pinion 19 is meshed with both of the first pulling rack 20 and the second pulling rack 21, and rotation of the pinion 19 is temporarily transmitted to both of the first pulling rack 20 and the second pulling rack 21 (the third transmission state).

In the embodiment, since the second pulling member 7 has the same flexible wire shape as the first pulling member 6, transmission of the force to the treatment section 3 using the second pulling member 7 uses a force of pulling the second pulling member 7. In the embodiment, the force of pressing the second pulling member 7 toward the treatment section 3 is not actively used for transmission of the energy for operating the treatment section 3 like the first pulling member 6.

Here, in a state in which the pinion 19 and the second pulling rack 21 are meshed with each other, if the pinion 19 and the first pulling rack 20 are meshed with each other, an operation in which the first pulling rack 20 presses the first pulling member 6 occurs simultaneously with the operation in which the second pulling rack 21 pulls the second pulling member 7. In the embodiment, in a state in which the pinion 19 and the second pulling rack 21 are meshed with each other, the first pulling rack 20 is parted from the pinion 19, and the first pulling rack 20 does not press the first pulling member 6. For this reason, the first pulling member 6 is prevented from deforming or unintentionally moving upon pulling of the second pulling member 7.

When the force is transmitted to the treatment section 3 from the second pulling member 7, the pulling force of the second pulling member 7 may be transmitted to the first pulling member 6 via the treatment section 3. In the embodiment, since the first pulling rack 20 and the pinion 19 are spaced from each other upon pulling of the second pulling member 7, when the pulling force of the second pulling member 7 is transmitted to the first pulling member 6 via the treatment section 3, the first pulling member 6 moves the first pulling rack 20 in the longitudinal direction of the first pulling rack 20 without receiving restriction from the pinion 19, Accordingly, the first pulling member 6 is configured hardly slacken.

In this way, in the embodiment, at a pulled member among the first pulling member 6 and the second pulling member 7, the driving force from the driving section 10 is reliably transmitted, and at a member in which the pulling is not needed, an effect of the driving force from the driving section 10 is not directly received. In addition, for example, when the first pulling member 6 is pulled, since there is no spring or the like to absorb the driving force from the driving section 10 to the treatment section 3, loss of the energy generated by the power source 11 is small. In addition, loss of the force is also small when the second pulling member 7 is pulled.

Since a transmission path of the power is switched in the switching section 15, there is no need to separately provide the power of pulling the first pulling rack 20 and the power of pulling the second pulling rack 21, and thus a configuration of the apparatus can be reduced in size.

Modified Example 1

Figure 9:
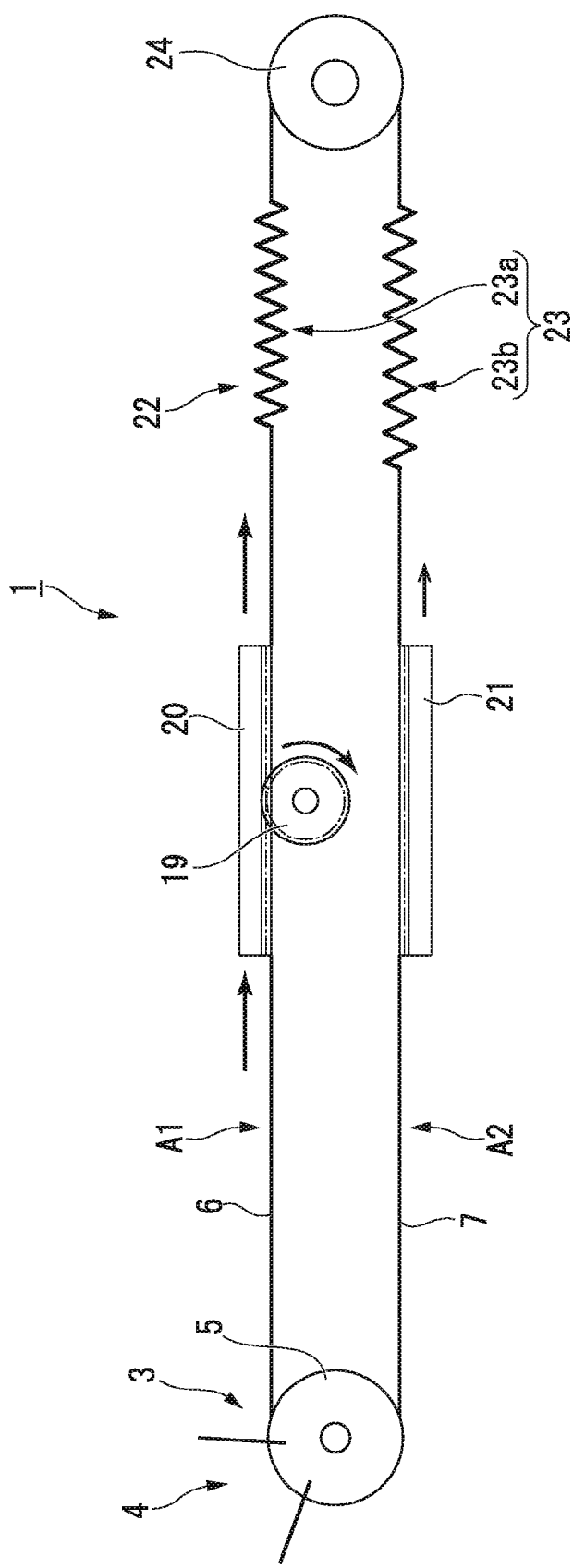
FIG. 9 is a schematic diagram showing a configuration of a modified example of the surgical instrument according to the first embodiment of the present invention.

Next, a modified example of the embodiment will be described. FIG. 9 is a schematic diagram showing a configuration of a modified example of the surgical instrument according to the embodiment.

As shown in FIG. 9, in the modified example, the switching section 15 described in the embodiment further includes a tension-applying section 22. The tension-applying section 22 applies tension to a first region A1 of the first pulling member 6 and a second region A2 of the second pulling member 7. The first region A1 is a region from a contact position of the first pulling member 6 and the first pulling rack 20 to the treatment section 3. The second region A2 is a region from a contact position of the second pulling member 7 between the second pulling member 7 and the second pulling rack 21 to the treatment section 3.

The tension-applying section 22 has biasing members 23 (a first biasing member 23a and a second biasing member 23b). The biasing members 23 apply biasing forces to independently move the first pulling member 6 and the second pulling member 7 toward the proximal end.

The first biasing member 23a is a tension spring fixed to the proximal end of the first pulling rack 20 and configured to pull the first pulling rack 20 to the proximal side. The second biasing member 23b is a tension spring fixed to the proximal end of the second pulling rack 21 and configured to pull the second pulling rack 21 to the proximal side.

A biasing force of the first biasing member 23a is set to a magnitude at which the first pulling rack 20 can be moved by the pinion 19 and the first pulling member 6 can be pulled until become a state that the first pulling member 6 has no slack in a state in which the power transmission path is cut by parting the pinion 19 from the first pulling rack 20. The biasing force of the second biasing member 23b is set to a magnitude at which the second pulling rack 21 can be moved by the pinion 19 and the second pulling member 7 can be pulled until become a state that the second pulling member 7 has no slack have no slack in a state in which the power transmission path is cut by parting the pinion 19 from the second pulling rack 21.

In the modified example, in addition to the first pulling member 6 or the second pulling member 7 not being pressed toward the treatment section 3, the slack is removed by the first biasing member 23a or the second biasing member 23b at an opposite member of one of the first pulling member 6 and the second pulling member 7 that transmits the force for operating the treatment section 3.

In addition, the first biasing member 23a and the second biasing member 23b are connected to each other via a pulley 24. Accordingly, the force applied to the first biasing member 23a is transmitted to the second biasing member 23b, and the force applied to the second biasing member 23b is transmitted to the first biasing member 23a.

For example, when each of the proximal ends of the first biasing member 23a and the second biasing member 23b are fixed, a load applied to the first biasing member 23a or the second biasing member 23b is increased according to an operation amount of the treatment section 3 when the treatment section 3 is largely operated. At this time, a large force may be difficult to apply to the treatment section 3 because the load applied to the first biasing member 23a or the second biasing member 23b serves as resistance. That is, tension in the first pulling member 6 or the second pulling member 7 is not constant.

On the other hand, in the modified example, since the first biasing member 23a and the second biasing member 23b are connected to each other via the pulley 24, the pulley 24 is rotated when the treatment section 3 is largely operated, thereby excessive load applied to the first biasing member 23a or the second biasing member 23b can be prevented. For this reason, even when the treatment section 3 is largely operated, the load applied to the first biasing member 23a or the second biasing member 23b becomes appropriate, and the force for operating the treatment section 3 is easily generated. That is, unlike the case in which each of the proximal ends of the first biasing member 23a and the second biasing member 23b is in a fixed state, in the modified example, since the tension in the first pulling member 6 or the second pulling member 7 is constant, operation characteristics of the treatment section 3 are improved. According to the modified example, since constant tension is applied as described above regardless of an angle of the treatment section 3, operation characteristics of the treatment section 3 are also improved in this point.

Modified Example 2

Next, another modified example of the embodiment will be described with reference to FIG. 10.

Figure 10:
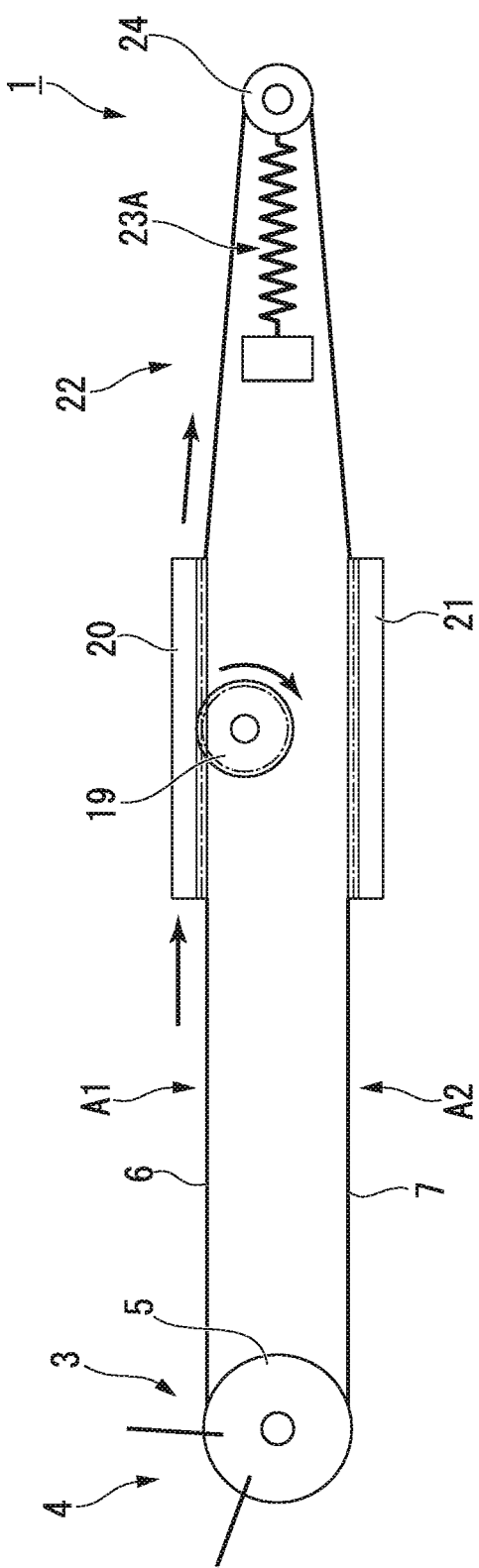
FIG. 10 is a schematic diagram showing a configuration of a second modified example of the surgical instrument according to the first embodiment of the present invention.

FIG. 10 is a schematic diagram showing a configuration of the modified example.

As shown in FIG. 10, in the modified example, instead of the first biasing member 23a and the second biasing member 23b being provided, the biasing member 23A configured to press the pulley 24 toward the proximal side is provided. In the modified example, the biasing member 23A is a compression spring to press the pulley 24 toward the proximal side.

In the above-mentioned configuration, the load is moved between the first pulling rack 20 side and the second pulling rack 21 side via the pulley 24, and a pulling force for removing the slack of the first pulling member 6 or the second pulling member 7 is applied by the biasing member 23A.

In addition, since the spring element is smaller than that of the modified example 1, a simple configuration can be provided.

Second Embodiment

Figure 11:
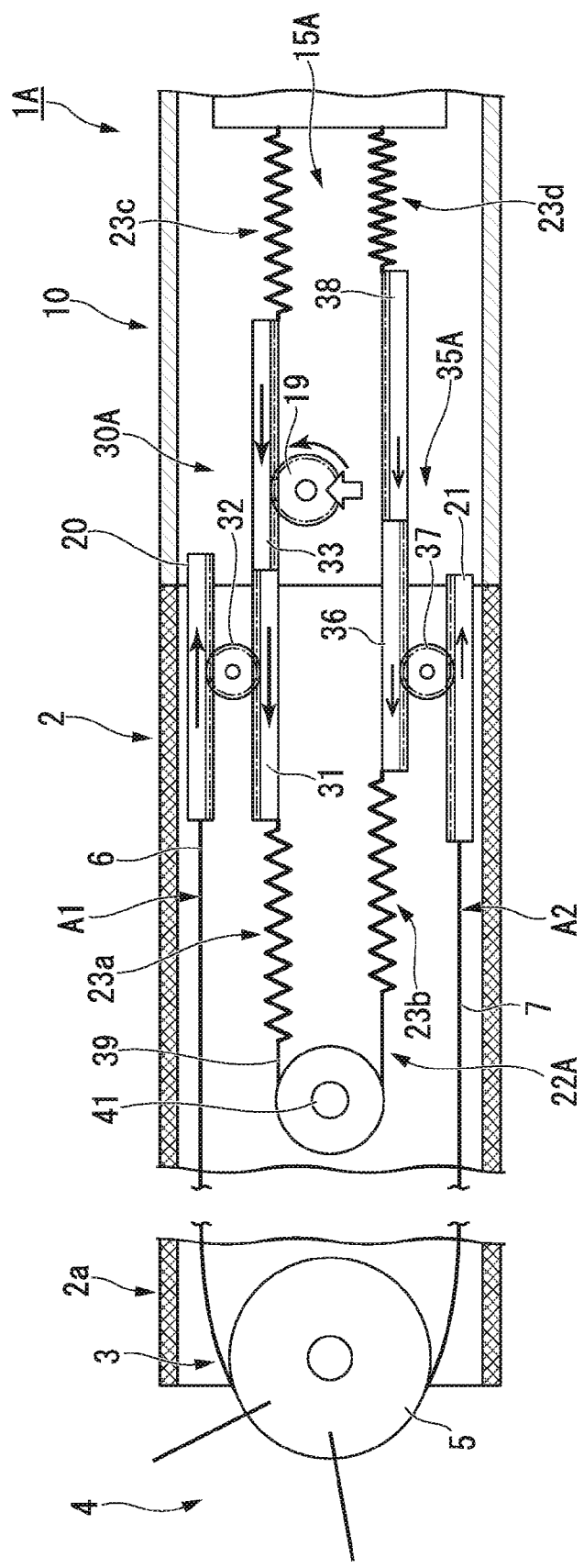
FIG. 11 is a schematic diagram showing a surgical instrument according to a second embodiment of the present invention.
Figure 12:
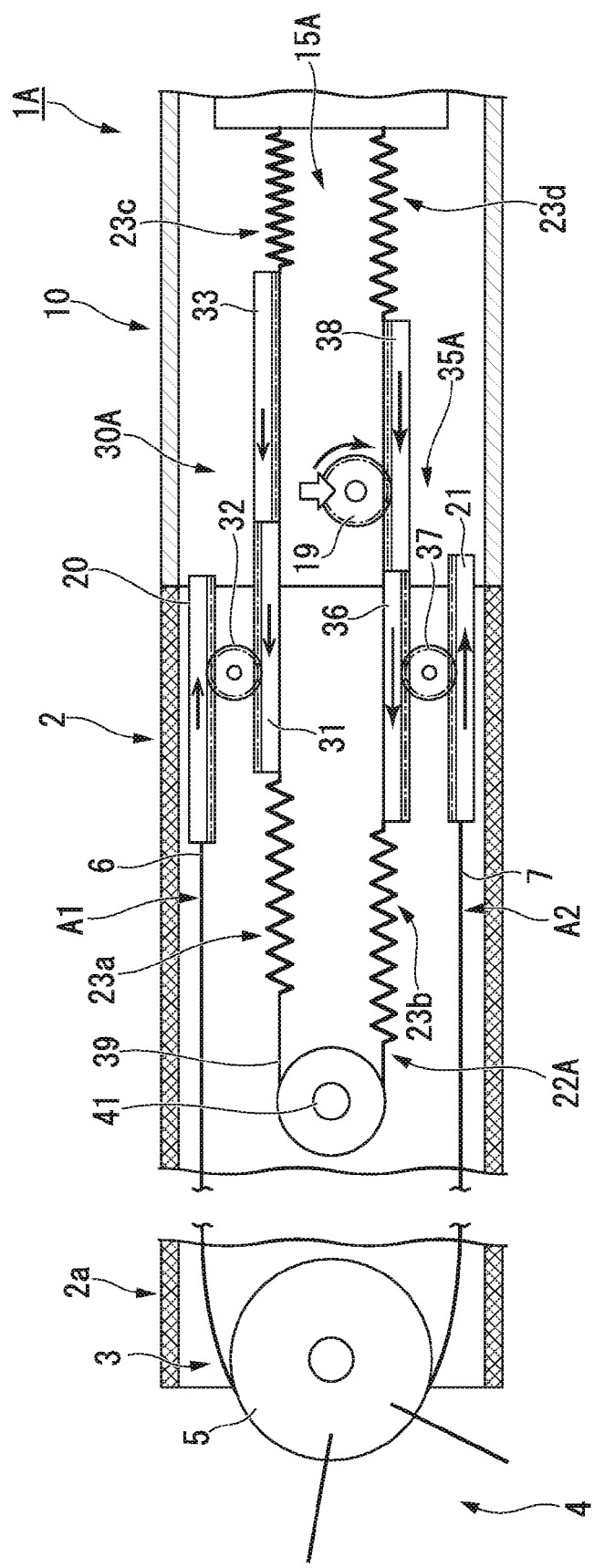
FIG. 12 is a view describing an action of the surgical instrument according to the second embodiment of the present invention.

Next, a second embodiment of the present invention will be described. FIG. 11 is a schematic diagram showing the surgical instrument 1A according to the embodiment. FIG. 12 is a view describing an action of the surgical instrument 1A according to the embodiment.

As shown in FIGS. 11 and 12, in the surgical instrument 1A according to the embodiment, the insertion section 2 and the driving section 10 can be separated from each other. Since the insertion section 2 has the distal end section 2a inserted into the body, the insertion section 2 is frequently sterilized. In addition, because the insertion section 2 should be compatible with various types of sterilization such as high-pressure steam sterilization, sterilization using ethylene oxide gas or the like, and so on, it is preferable that an electronic instrument, a circuit, or the like is not disposed at the insertion section 2. On the other hand, since no portion of the driving section 10 is inserted into the body, it is sufficient for the driving section 10 to be covered with a sterilized drape.

The surgical instrument 1A according to the embodiment has a switching section 15A having a different configuration, instead of the switching section 15 described in the first embodiment.

The switching section 15A has a first rack section 30A and a second rack section 35A having different configurations from the first rack section and the second rack section described in the first embodiment.

The first rack section 30A has the first pulling rack 20, a first facing rack 31, a first gear 32 and a first pressing rack 33. The first pulling member 6 is fixed to the first pulling rack 20. The first facing rack 31 has teeth facing teeth of the first pulling rack 20 and is disposed parallel to the first pulling rack 20. The first gear 32 is configured to be meshed with both of the first pulling rack 20 and the first facing rack 31 to connect the first pulling rack 20 and the first facing rack 31. The first pressing rack 33 is configured to be meshed with the pinion 19 described in the first embodiment and to be capable of advancing and retracting in the longitudinal direction of the first facing rack 31 by the pinion 19.

The first pressing rack 33 is configured such that a distal end of the first pressing rack 33 abuts a proximal end of the first facing rack 31 due to a biasing force of a first biasing member 23c. The first pressing rack 33 need not be fixed to the first facing rack 31. That is, in the embodiment, separation of the insertion section 2 and the driving section 10 is accomplished by the first pressing rack 33 and the first facing rack 31 being separable from each other.

The first gear 32 always connects the first pulling rack 20 and the first facing rack 31. A moving direction of the first pulling rack 20 is configured to oppose the moving direction of the first facing rack 31 by the first gear 32.

The second rack section 35A has the second pulling rack 21, a second facing rack 36, a second gear 37 and a second pressing rack 38. The second pulling member 7 is fixed to the second pulling rack 21. The second facing rack 36 has teeth facing teeth of the second pulling rack 21 and is disposed parallel to the second pulling rack 21. The second gear 37 is configured to mesh with both of the second pulling rack 21 and the second facing rack 36 to connect the second pulling rack 21 and the second facing rack 36. The second pressing rack 38 is configured to mesh with the pinion 19 described in the first embodiment and to be capable of advancing and retracting in the longitudinal direction of the second facing rack 36 by the pinion 19.

The second pressing rack 38 is configured such that a distal end of the second pressing rack 38 abuts a proximal end of the second facing rack 36 due to a biasing force of a second biasing member 23d. The second pressing rack 38 need not be fixed to the second facing rack 36. That is, in the embodiment, separation of the insertion section 2 and the driving section 10 is accomplished by the second pressing rack 38 and the second facing rack 36 being separable from each other.

The second gear 37 always connects the second pulling rack 21 and the second facing rack 36. A moving direction of the second pulling rack 21 is configured to oppose a moving direction of the second facing rack 36 by the second gear 37.

Instead of the tension-applying section 22 described in the first embodiment, a tension-applying section 22A connected to the first facing rack 31 and the second facing rack 36 is provided with the surgical instrument 1A according to the embodiment. The tension-applying section 22A has the first biasing member 23a and the second biasing member 23b. The first biasing member 23a is connected to the distal end of the first facing rack 31. The second biasing member 23b is connected to the distal end of the second facing rack 36. The distal ends of the first biasing member 23a and the second biasing member 23b are connected by a connecting wire 39 disposed to be turned down by a pulley 41.

Since the first pulling rack 20 is moved toward the distal side by pulling the first facing rack 31 to the proximal side by the first biasing member 23a, and the second pulling rack 21 is moved toward the distal side by pulling the second facing rack 36 toward the proximal side by the second biasing member 23b, the tension-applying section 22A according to the embodiment has the same action as that of the first embodiment.

Next, an action of the surgical instrument 1A according to the embodiment will be described.

As shown in FIG. 11, in the surgical instrument 1A according to the embodiment, when the pinion 19 is engaged with the first pressing rack 33 and the first pressing rack 33 presses the proximal end of the first facing rack 31 due to rotation of the pinion 19, the first pressing rack 33 moves the first facing rack 31 toward the distal side. The first facing rack 31 rotates the first gear 32 and the first gear 32 moves the first pulling rack 20 fixed to the first pulling member 6 toward the proximal side. Accordingly, in the surgical instrument 1A according to the embodiment, when the first pressing rack 33 is moved toward the distal side, the first pulling member 6 is pulled toward the proximal side.

In a process in which the first pressing rack 33 moves toward the distal side, since the pinion 19 is spaced from the second pressing rack 38, a force moving the second pressing rack 38 is not transmitted from the pinion 19. For this reason, a force moving the second pulling member 7 toward the distal side is not applied. Further, since the second biasing member 23b of the tension-applying section 22A continuously applies the tension to the second pulling member 7, the slack of the second pulling member 7 is removed.

In addition, as shown in FIG. 12, when the pinion 19 is engaged with the second pressing rack 38 and the second pressing rack 38 presses the proximal end of the second facing rack 36 by rotation of the pinion 19, the second pressing rack 38 moves the second facing rack 36 toward the distal side. The second facing rack 36 rotates the second gear 37, and the second pulling rack 21 fixed to the second pulling member 7 moves the second gear 37 toward the proximal side. Accordingly, in the surgical instrument 1A according to the embodiment, when the second pressing rack 38 is moved toward the distal side, the second pulling member 7 is pulled toward the proximal side.

In the process in which the second pressing rack 38 is moved toward the distal side, since the pinion 19 is spaced from the first pressing rack 33, a force moving the first pressing rack 33 is not transmitted from the pinion 19. For this reason, a force moving the first pulling member 6 toward the distal side is not applied. Further, since the first biasing member 23a of the tension-applying section 22A continuously applies the tension to the first pulling member 6, the slack of the first pulling member 6 is removed.

Modified Example

Figure 13:
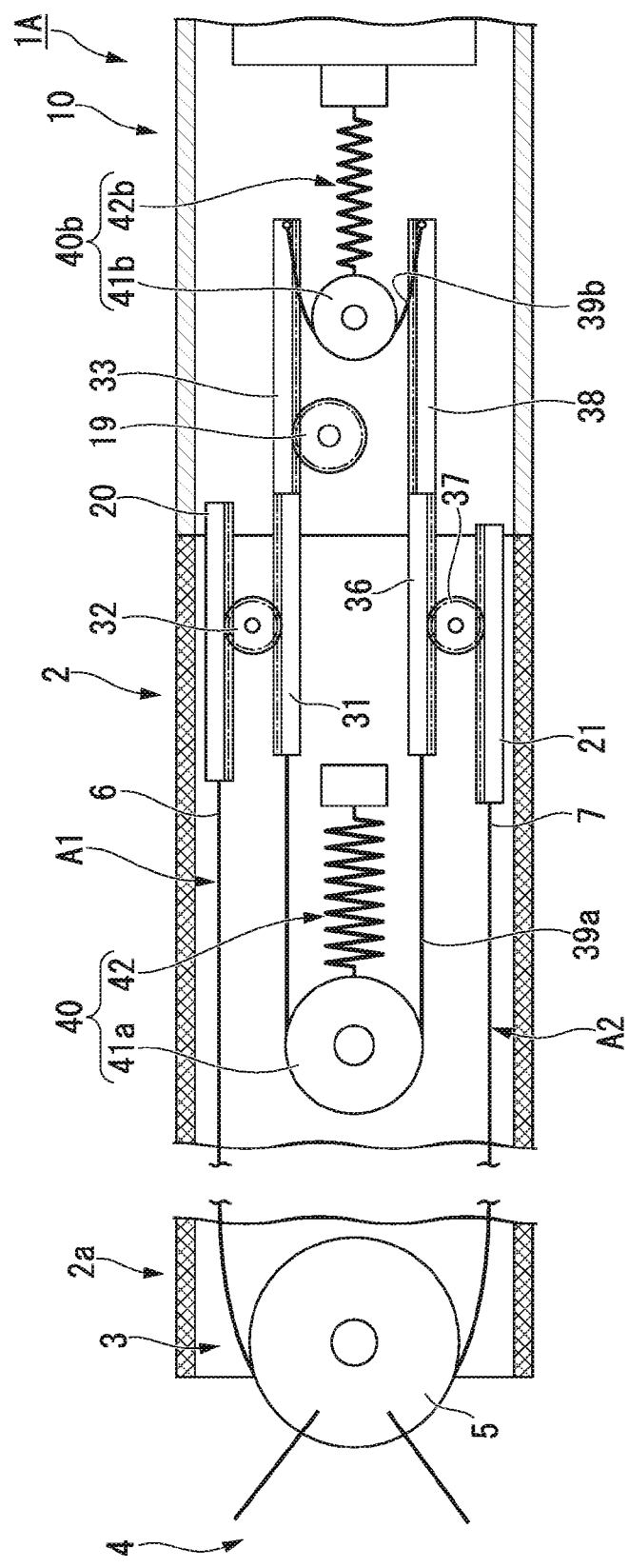
FIG. 13 is a schematic diagram showing a configuration of a modified example of the surgical instrument according to the second embodiment of the present invention.

Next, a modified example of the embodiment will be described. FIG. 13 is a schematic diagram showing a configuration of a modified example of the surgical instrument according to the embodiment.

In the modified example, instead of the tension-applying section 22A as shown in FIG. 11 which includes the first biasing member 23a and the second biasing member 23b, as shown in FIG. 13, a connecting wire 39a configured to connect the first facing rack 31 and the second facing rack 36 and a spring section 40 configured to apply tension to the connecting wire 39a are installed.

The spring section 40 has a pulley 41a which is hooked the connecting wire 39a on an outer circumferential surface, and a compression spring 42 pressing the pulley 41a toward the distal end side.

While in the configuration described in the second embodiment, two biasing elements of the first biasing member 23a and the second biasing member 23b are provided, the modified example can realize the same advantage in the case using the first biasing member 23a and the second biasing member 23b described in the second embodiment, by one biasing element, that is, the spring section 40.

As shown in FIG. 13, the modified example includes a connecting wire 39b connecting the first pressing rack 33 and the second pressing rack 38, and a spring section 40b pressing the connecting wire 39b toward the distal side. That is, in the modified example, the spring section 40b acts to move the first pressing rack 33 and the second pressing rack 38 toward the distal side. The spring section 40b has the pulley 41b and the compression spring 42b like the spring section 40 of the second embodiment.

When the insertion section 2 and the driving section 10 of the surgical instrument 1A are separated, the first pressing rack 33 is spaced from the first facing rack 31, and the second pressing rack 38 is spaced from the second facing rack 36. For this reason, when the insertion section 2 and the driving section 10 of the surgical instrument 1A are separated, both of the first pressing rack 33 and the second pressing rack 38 are moved toward the distal side by a biasing force transmitted to the first pressing rack 33 and the second pressing rack 38 by the spring section 40b.

When the insertion section 2 and the driving section 10 of the surgical instrument 1A are attached, the spring section 40b presses the first pressing rack 33 against the proximal end of the first facing rack 31 and presses the second pressing rack 38 against the proximal end of the second facing rack 36.

In the operation of the surgical instrument 1A in which the pinion 19 is rotated, a force moving one of the first facing rack 31 and the second facing rack 36 with which the pinion 19 is not engaged toward the distal end side by the compression spring 42 of the spring section 40 is transmitted, and the slack of one of the first pulling member 6 and the second pulling member 7 that does not contribute to the pulling operation of the treatment section 3 is removed like the tension-applying section 22A described in the second embodiment.

Third Embodiment

Figure 14:
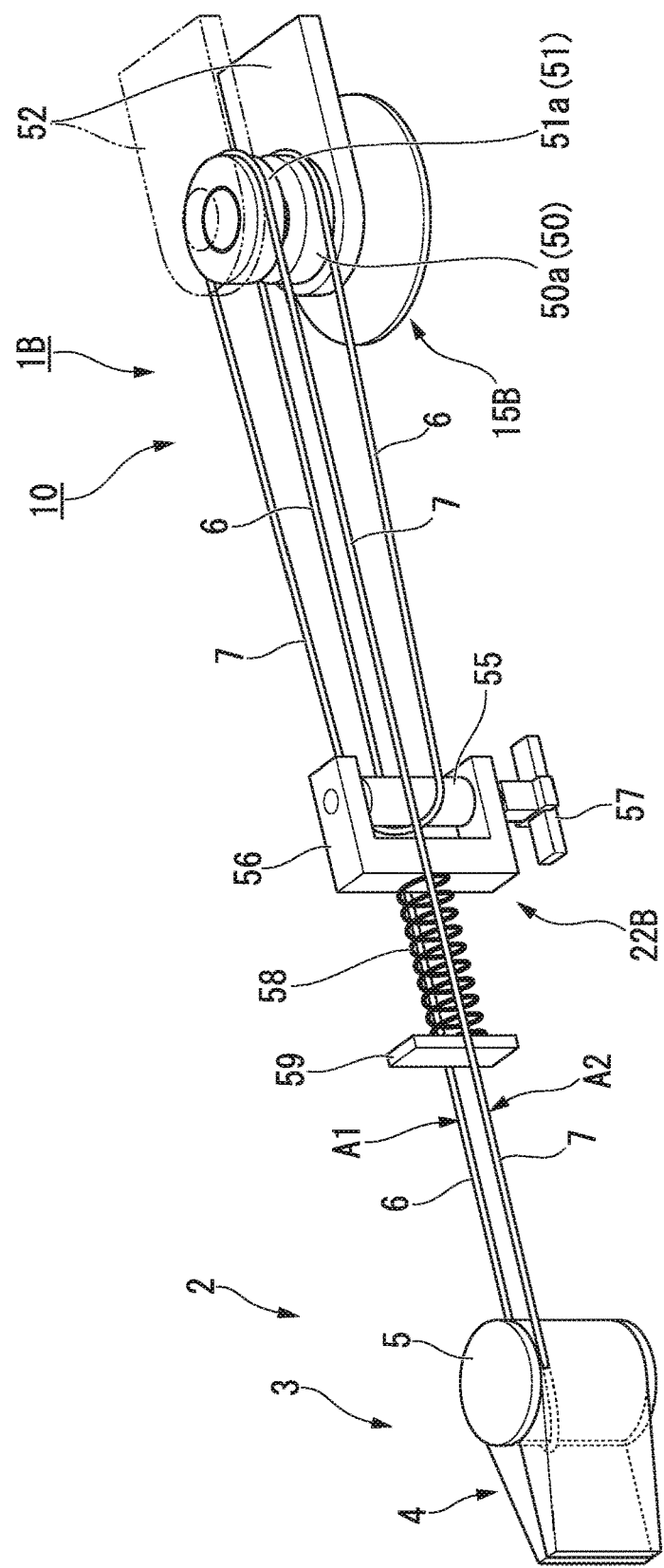
FIG. 14 is a schematic diagram showing a surgical instrument according to a third embodiment of the present invention.
Figure 15:
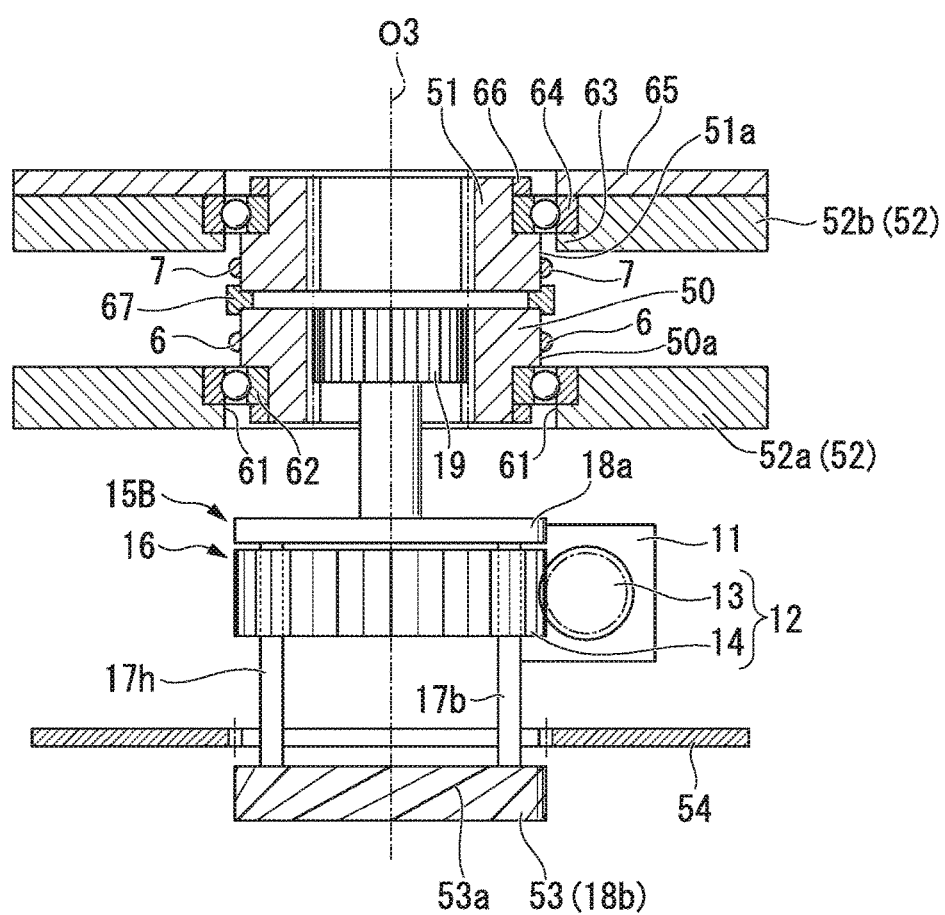
FIG. 15 is a schematic diagram showing a driving section of the surgical instrument according to the third embodiment of the present invention.

Next, a third embodiment of the present invention will be described. FIG. 14 is a perspective view schematically showing the surgical instrument according to the embodiment. FIGS. 15 and 16 are schematic diagrams showing the driving section of the surgical instrument.

As shown in FIGS. 14, 15 and 16, instead of the switching section 15 described in the first embodiment, a surgical instrument 1B according to the embodiment has a switching section 15B having a different configuration from the switching section 15 of the first embodiment. In addition, in the embodiment, the first pulling member 6 and the second pulling member 7 are constituted by a series of linear members.

In the switching section 15B, a first internal gear 50 is provided as a first engaging body instead of the first pulling rack 20 described in the first embodiment, and a second internal gear 51 is provided as a second engaging body instead of the second pulling rack 21 described in first embodiment. The first internal gear 50 has an outer circumferential surface 50a with which the first pulling member 6 is frictionally engaged. The second internal gear 51 has an outer circumferential surface 51a with which the second pulling member 7 is frictionally engaged.

The first pulling member 6 and the second pulling member 7 are connected via a tension-applying section 22B to obtain the same effect as the tension-applying section 22 according to the modified example of the first embodiment.

The tension-applying section 22B includes a pulley 55, a pulley holding section 56, a guide 57, a spring 58 and a support section 59. A linear member that constitutes the first pulling member 6 and the second pulling member 7 is wound on an outer circumferential surface of the pulley 55. The pulley holding section 56 rotatably holds the pulley 55. The guide 57 slidably holds the pulley holding section 56 in a direction in which the distal end and the proximal end in the driving section 10 are connected. The spring 58 is disposed at the distal side of the pulley holding section 56 and installed to press the pulley holding section 56 toward the proximal side. The support section 59 supports the distal end of the spring 58.

The spring 58 moves the pulley holding section 56 along the guide 57 such that a constant tension is applied to the linear member that constitutes the first pulling member 6 and the second pulling member 7, and holds the pulley holding section 56 at a position at which a constant tension is applied to the linear member that constitutes the first pulling member 6 and the second pulling member 7.

The tension-applying section 22B of the embodiment is different from the first embodiment in that, an end of the first pulling member 6 opposite to a connecting end with respect to the treatment section 3 is pulled toward the distal end side of the surgical instrument 1B rather than the proximal end of the surgical instrument 1B by hooking the first pulling member 6 on the outer circumferential surface 50a of the first internal gear 50. Similarly, the tension-applying section 22B of the embodiment is different from that of the first embodiment in that, an end of the second pulling member 7 opposite to the connecting end with respect to the treatment section 3 is pulled toward the distal end side of the surgical instrument 1 rather than the proximal end side of the surgical instrument 1B by hooking the second pulling member 7 on the outer circumferential surface 51a of the second internal gear 51.

As shown in FIGS. 15 and 16, the first internal gear 50 and the second internal gear 51 are independently rotatable with each other about the same rotational center O3 with respect to each other, and each of the first internal gear 50 and the second internal gear 51 can be meshed with the pinion 19. Specifically, the switching section 15B has a gear case 52 configured to accommodate both of the first internal gear 50 and the second internal gear 51 therein.

The gear case 52 has a first support section 61, a second support section 63, a first holding member 65 and a second holding member 66. The first support section 61 is connected to the first internal gear 50 via a bearing 62. The second support section 63 is connected to the second internal gear 51 via a bearing 64. The first holding member 65 and the second holding member 66 are installed to hold the bearing 64.

The first support section 61 and the second support section 63 are disposed to have a fixed positional relation in a state in which a gap is formed therebetween by a washer 67 such that both of the first internal gear 50 and the second internal gear 51 are accommodated between the first support section 61 and the second support section 63. The gear case 52 forms a holding section configured to hold the first internal gear 50 and the second internal gear 51 such that the first internal gear 50 and the second internal gear 51 can be independently rotated about the same rotational center.

In the embodiment, the bearing 62 and the bearing 64 are constituted by ball bearings.

A ring of an outer circumferential side of the bearing 62 is fitted into the first support section 61. A ring of an inner circumferential side of the bearing 62 is fitted into the first internal gear 50 through threaded engagement.

A ring of an outer circumferential side of the bearing 64 is fitted to the second support section 63 and is covered by the first holding member 65. The first holding member 65 is fixed to the second support section 63 by, for example, adhesion or the like. A ring of an inner circumferential side of the bearing 64 is covered by the second holding member 66 simultaneously with fitting to the second internal gear 51.

The second holding member 66 is fitted to the second internal gear 51 through threaded engagement.

The first internal gear 50 and the second internal gear 51 are held by the gear case 52 via ball bearings (the bearings 62 and 64). For this reason, sliding resistance when the first internal gear 50 and the second internal gear 51 are rotated is small. In addition, in the embodiment, the first internal gear 50 and the second internal gear 51 in a state in which the bearings 62 and 64 are fitted and the washer 67 is interposed therebetween are accommodated in the gear case 52 and then covered by the first holding member 65. As a result, the first internal gear 50 and the second internal gear 51 can be easily incorporated into the gear case 52.

In the embodiment, in a state in which the first internal gear 50 is meshed with the pinion 19, the second internal gear 51 is spaced from the pinion 19. In a state in which the second internal gear 51 is meshed with the pinion 19, the first internal gear 50 is spaced from the pinion 19. Accordingly, in the embodiment, a state (a first transmission state) in which power is transmitted from the power source 11 to the first pulling member 6 as shown in FIG. 15 and a state (a second transmission state) in which power is transmitted from the power source 11 to the second pulling member 7 as shown in FIG. 16 are exclusively selected by movement of the pinion 19.

The switching section 15B has a cam plate 53 and a support hole section 54 as a mechanism to move the second end section member 18b of the moving section 16, instead of the disk (the second end section member 18b), the connecting section and the actuator (neither of which is shown) described in the first embodiment.

The cam plate 53 is formed in a disk shape to be rotatable about the rotational center O3 of the worm wheel 14. A plurality of inclined convex sections 53a that form a spiral shape about a rotational center of the cam plate 53 are formed on an outer circumferential surface of the cam plate 53. That is, the plurality of inclined convex sections 53a inclined with respect to a rotational center axis of the cam plate 53 are formed at the outer circumferential surface of the cam plate 53. In the embodiment, the inclined convex section 53a of the cam plate 53 is multiple threads, and the support hole section 54 is a multi-threaded nut meshed with the inclined convex section 53a.

The support hole section 54 is a hole having a concavo-convex shape with which the inclined convex section 53a of the cam plate 53 is engaged. In the embodiment, the support hole section 54 is fixed to a housing (not shown) of the driving section 10.

The rotational center of the cam plate 53 is coaxial with the rotational center O3 of the first internal gear 50 and the second internal gear 51. Since the support hole section 54 and the cam plate 53 are engaged with each other, when the cam plate 53 is rotated about the rotational center of the cam plate 53 in a state in which the cam plate 53 is engaged with the support hole section 54, the cam plate 53 advances and retracts in the axial direction of the rotational center O3 of the cam plate 53 by a rotating force of the cam plate 53.

A relation between a rotation direction of the cam plate 53 and an advance and retract moving direction of the cam plate 53 is configured such that the cam plate 53 pushes the pinion 19 toward the first internal gear 50 when the pinion 19 is rotated in a direction in which the first pulling member 6 is pulled by the first internal gear 50. The relation between the rotation direction of the cam plate 53 and the advance and retract moving direction of the cam plate 53 is configured such that the cam plate 53 pushes the pinion 19 toward the second internal gear 51 when the pinion 19 is rotated in a direction in which the second pulling member 7 is pulled by the second internal gear 51.

In the embodiment, as in the first embodiment, a configuration of moving the worm wheel 14 using the actuator (for example, the actuator 25 shown in FIG. 5) may be employed.

An action of the surgical instrument 1B according to the embodiment will be described.

In the embodiment, a mesh of the pinion 19 and the first internal gear 50 and a mesh of the pinion 19 and the second internal gear 51 are switched due to the advance and retract operation of the pinion 19 by the cam plate 53 and the support hole section 54 by using a portion of the power of the servo motor of rotating the worm wheel 14. For this reason, the power is transmitted to only the first pulling member 6 when the worm wheel 14 is rotated to pull the first pulling member 6, and the power is transmitted to only the second pulling member 7 when the worm wheel 14 is rotated to pull the second pulling member 7.

In the embodiment, as in the modified example of the first embodiment, the slack of an opposite side of one of the first pulling member 6 and the second pulling member 7 to which the force for pulling the treatment section 3 is applied is removed by the tension-applying section 22B.

While exemplary embodiments of the present invention have been described above, the present invention is not limited to these embodiments. Additions, omissions, substitutions and other modifications may be made without departing from the spirit of the present invention.

For example, while the pinion 19 is configured to move on a rotational center axis thereof serving as the switching section in these embodiments, the rotational center axis of the pinion 19 may be configured to move horizontally as shown in FIGS. 7, 8, 11 and 12.

In the second embodiment, the first pulling rack 20 and the first facing rack 31 need not be parallel to each other, and the second pulling rack 21 and the second facing rack 36 need not be parallel to each other.

In the third embodiment, the first pulling member 6 and the second pulling member 7 may be separate bodies. In this case, the distal end section of the first pulling member 6 may be wound on the outer circumferential surface of the first internal gear 50, and the distal end section of the second pulling member 7 may be wound and connected to the outer circumferential surface of the second internal gear 51.

While embodiments of the present invention have been described above, the technical range of the present invention is not limited to these embodiments, but combinations of components of the embodiments may be modified, and various changes may be added to the components or may be removed without departing from the spirit of the present invention. The present invention is not limited by the above-mentioned description but is limited by the range of the accompanying claims.

What is claimed is:

1. A surgical instrument, comprising:
   a treatment section configured to treat a treatment target;
   a first pulling section configured to transmit a pulling force to the treatment section to operate the treatment section;
   a second pulling section configured to transmit a pulling force to the treatment section to operate the treatment section;
   a power source configured to generate force for operating the treatment section; and
   a switching section having a first path configured to transmit the force from the power source to the first pulling section and a second path configured to transmit the force from the power source to the second pulling section and the switching section being configured to switch the first path and the second path.

2. The surgical instrument according to claim 1, wherein the first pulling section has a first pulling member that is flexible and connected to the treatment section,
   the second pulling section has a second pulling member that is flexible and connected to the treatment section, and
   the switching section has:
      a first engaging body to which the first pulling member is connected; and
      a second engaging body to which the second pulling member is connected.

3. The surgical instrument according to claim 2, wherein the switching section has a tension-applying section configured to apply common tension to a first region in the first pulling member from a contact position of the first pulling member and the first engaging body to the treatment section, and a second region in the second pulling member from a contact position of the second pulling member and the second engaging body to the treatment section.

4. The surgical instrument according to claim 3, wherein the first engaging body is a first rack section to which the first pulling member is fixed,
   the second engaging body is a second rack section to which the second pulling member is fixed,
   the switching section has:
      a pinion configured to be capable of meshing with the first rack section and the second rack section;
      a moving section configured to move the pinion to switch between a first transmission state and a second transmission state, the first transmission state in which the pinion is meshed with the first rack section and the pinion is spaced from the second rack section, and the second transmission state in which the pinion is meshed with the second rack section and the pinion is spaced from the first rack section; and
      a transmission section configured to transmit the force from the power source to the pinion,
   the first rack section has:
      a first pulling rack to which the first pulling member is fixed;
      a first facing rack having teeth facing teeth of the first pulling rack and disposed parallel to the first pulling rack;
      a first gear configured to mesh with both of the first pulling rack and the first facing rack so as to connect the first pulling rack and the first facing rack; and
      a first pressing rack configured to be capable of meshing with the pinion and configured to be capable of advancing and retracting in a longitudinal direction of the first facing rack due to the pinion, and configured to press the first facing rack such that the first facing rack moves in a longitudinal direction of the first facing rack,
   the second rack section has:
      a second pulling rack to which the second pulling member is fixed;
      a second facing rack having teeth facing teeth of the second pulling rack and disposed parallel to the second pulling rack;
      a second gear configured to mesh both of the second pulling rack and the second facing rack so as to connect the second pulling rack and the second facing rack; and
      a second pressing rack configured to be capable of meshing with the pinion and configured to be capable of advancing and retracting in a longitudinal direction of the second facing rack due to the pinion, and configured to press the second facing rack such that the second facing rack moves in the longitudinal direction of the second facing rack, and
   the tension-applying section connects the first facing rack and the second facing rack.

5. The surgical instrument according to claim 3, wherein the first engaging body is a first internal gear having an outer circumferential surface with which the first pulling member is frictionally engaged,
   the second engaging body is a second internal gear having an outer circumferential surface with which the second pulling member is frictionally engaged, and
   the switching section has:
      a holding section configured to hold the first internal gear and the second internal gear such that the first internal gear and the second internal gear are independently rotatable about the same rotational center;
      a pinion configured to be capable of meshing with the first internal gear and the second internal gear;
      a moving section configured to move the pinion between a first transmission state and a second transmission state, the first transmission state in which the pinion is meshed with the first internal gear and the pinion is separated from the second internal gear, the second transmission state in which the pinion is meshed with the second internal gear and the pinion is separated from the first internal gear; and
      a transmission section configured to transmit the force from the power source to the pinion.

6. The surgical instrument according to claim 5, wherein the moving section has a third transmission state in which the pinion is simultaneously meshed with both of the first engaging body and the second engaging body, and switching between the first transmission state and the second transmission state is performed via the third transmission state.

7. The surgical instrument according to claim 2, wherein the first engaging body is a first rack section to which the first pulling member is fixed,
the second engaging body is a second rack section to which the second pulling member is fixed, and
the switching section has:
a pinion configured to be capable of meshing with the first rack section and the second rack section;
a moving section configured to move the pinion to switch between a first transmission state and a second transmission state, the first transmission state in which the first rack section is meshed with the pinion and the second rack section is spaced from the pinion, the second transmission state in which the second rack section is meshed with the pinion and the first rack section is spaced from the pinion; and
a transmission section configured to transmit the force from the power source to the pinion.

8. The surgical instrument according to claim 7, wherein the first rack section has:
a first pulling rack to which the first pulling member is fixed;
a first facing rack having teeth facing teeth of the first pulling rack and disposed parallel to the first pulling rack;
a first gear configured to be meshed with both of the first pulling rack and the first facing rack so as to connect the first pulling rack and the first facing rack; and
a first pressing rack configured to be capable of meshing with the pinion, and configured to be capable of advancing and retracting in a longitudinal direction of the first facing rack by the pinion, and configured to press the first facing rack such that the first facing rack moves along the longitudinal direction of the first facing rack, and
the second rack section has:
a second pulling rack to which the second pulling member is fixed;
a second facing rack having teeth facing teeth of the second pulling rack and disposed parallel to the second pulling rack;
a second gear configured to be meshed with both of the second pulling rack and the second facing rack so as to connect the second pulling rack and the second facing rack; and
a second pressing rack configured to be capable of meshing with the pinion, and configured to be capable of advancing and retracting in a longitudinal direction of the second facing rack by the pinion, and configured to press the second facing rack such that the second facing rack moves along the longitudinal direction of the second facing rack.

9. The surgical instrument according to claim 7, wherein the moving section has a third transmission state in which the pinion is simultaneously meshed with both of the first engaging body and the second engaging body, and switching between the first transmission state and the second transmission state is performed via the third transmission state.

10. The surgical instrument according to claim 2, wherein the first engaging body is a first internal gear having an outer circumferential surface with which the first pulling member is frictionally engaged,
the second engaging body is a second internal gear having an outer circumferential surface with which the second pulling member is frictionally engaged, and
the switching section has:
a holding section configured to hold the first internal gear and the second internal gear such that the first internal gear and the second internal gear are independently rotatable about the same rotational center;
a pinion configured to be capable of meshing with the first internal gear and the second internal gear;
a moving section configured to move the pinion between a first transmission state and a second transmission state, the first transmission state in which the pinion is meshed with the first internal gear and the pinion is separated from the second internal gear, the second transmission state in which the pinion is meshed with the second internal gear and the pinion is separated from the first internal gear; and
a transmission section configured to transmit the force from the power source to the pinion.

11. The surgical instrument according to claim 10, wherein the moving section has a third transmission state in which the pinion is simultaneously meshed with both of the first engaging body and the second engaging body, and switching between the first transmission state and the second transmission state is performed via the third transmission state.

12. The surgical instrument according to claim 1, wherein the first pulling section and the second pulling section are a series of flexible linear members connected at proximal ends thereof.

13. A surgical instrument, comprising:
an end-effector configured to treat a treatment target;
a first elongated driving force transmission member configured to transmit a driving force to the end-effector to operate the end-effector;
a second elongated driving force transmission member configured to transmit the driving force to the end-effector to operate the end-effector;
an actuator configured to generate the driving force for operating the end- effector; and
one or move movable bodies configured to switch between a first transmission state in which the one or more movable bodies engage the actuator to transmit the driving force to the first elongated driving force transmission member and a second transmission state in which the one or more movable bodies engage the actuator to transmit the driving force to the second elongated driving force transmission member.

14. The surgical instrument according to claim 13, wherein:
the first elongated driving force transmission member has a first wire that is flexible and connected to the end-effector,
the second elongated driving force transmission member has a second wire that is flexible and connected to the end-effector, and
the one or more movable bodies has:
a first engaging body to which the first wire is connected; and
a second engaging body to which the second wire is connected.

15. The surgical instrument according to claim 14, wherein the first wire and the second wire comprise a series of flexible wires connected at proximal ends thereof.

16. The surgical instrument according to claim 14, wherein the one or more movable bodies further comprises a tension-applying spring configured to apply common tension to a first region in the first wire from a contact position of the first wire and the first engaging body to the end-effector, and a second region in the second wire from a contact position of the second wire and the second engaging body to the end-effector.

17. The surgical instrument according to claim 14, wherein the first engaging body is a first rack to which the first wire is fixed,
the second engaging body is a second rack to which the second wire is fixed, and
the one or more movable bodies comprise:
a pinion configured to be capable of meshing with the first rack and the second rack;
a moving body configured to move the pinion to switch between a first transmission state and a second transmission state, the first transmission state in which the first rack is meshed with the pinion and the second rack is spaced from the pinion, the second transmission state in which the second rack is meshed with the pinion and the first rack is spaced from the pinion; and
a transmission configured to transmit the force from the actuator to the pinion.

18. The surgical instrument according to claim 17, wherein the moving body has a third transmission state in which the pinion is simultaneously meshed with both of the first engaging body and the second engaging body, and switching between the first transmission state and the second transmission state is performed via the third transmission state.

19. The surgical instrument according to claim 14, wherein the first engaging body is a first internal gear having an outer circumferential surface with which the first wire is frictionally engaged,
the second engaging body is a second internal gear having an outer circumferential surface with which the second wire is frictionally engaged, and
the one or more movable bodies comprise:
a pulley configured to hold the first internal gear and the second internal gear such that the first internal gear and the second internal gear are independently rotatable about the same rotational center;
a pinion configured to be capable of meshing with the first internal gear and the second internal gear;
a moving body configured to move the pinion between a first transmission state and a second transmission state, the first transmission state in which the pinion is meshed with the first internal gear and the pinion is separated from the second internal gear, the second transmission state in which the pinion is meshed with the second internal gear and the pinion is separated from the first internal gear; and
a transmission configured to transmit the force from the actuator to the pinion.

20. The surgical instrument according to claim 19, wherein the moving body has a third transmission state in which the pinion is simultaneously meshed with both of the first engaging body and the second engaging body, and switching between the first transmission state and the second transmission state is performed via the third transmission state.

* * * * *